(12) United States Patent
Gill et al.

(10) Patent No.: US 11,987,605 B2
(45) Date of Patent: May 21, 2024

(54) MUTANT MYC FUSION POLYPEPTIDES AND USES THEREOF

(71) Applicant: Helix Nanotechnologies Inc, Boston, MA (US)

(72) Inventors: Taylor Gill, Cambridge, MA (US); Hannu Rajaniemi, Corte Madera, CA (US); Nikolai Eroshenko, Boston, MA (US)

(73) Assignee: Helix Nanotechnologies Inc, Boston, MA (US)

( * ) Notice: Subject to any disclaimer, the term of this patent is extended or adjusted under 35 U.S.C. 154(b) by 0 days.

(21) Appl. No.: 17/025,717

(22) Filed: Sep. 18, 2020

(65) Prior Publication Data

US 2021/0107955 A1 Apr. 15, 2021

Related U.S. Application Data

(60) Provisional application No. 62/902,526, filed on Sep. 19, 2019.

(51) Int. Cl.
| | |
|---|---|
| *C07K 14/47* | (2006.01) |
| *C12N 5/10* | (2006.01) |
| *C12N 5/16* | (2006.01) |
| *C12N 15/63* | (2006.01) |

(52) U.S. Cl.
CPC ............ *C07K 14/4703* (2013.01); *C12N 5/10* (2013.01); *C12N 5/16* (2013.01); *C12N 15/63* (2013.01); *C07K 2319/09* (2013.01); *C07K 2319/70* (2013.01); *C12N 2330/50* (2013.01)

(58) Field of Classification Search
CPC ................... C07K 14/4703; C07K 2319/80
See application file for complete search history.

(56) References Cited

U.S. PATENT DOCUMENTS

| | | | |
|---|---|---|---|
| 2004/0170619 A1* | 9/2004 | Girdlestone ............ | C12N 15/86 435/199 |
| 2005/0032186 A1* | 2/2005 | Kim ........................ | A61P 17/06 435/6.12 |
| 2022/0152179 A1* | 5/2022 | Soucek ................... | A61K 45/06 |

OTHER PUBLICATIONS

GenBank Accession No. A1YG22.1, publicly available Sep. 12, 2018, printed as pp. 1/4-4/4. (Year: 2018).*
GenBank Accession No. NP_001280157.1, publicly available Aug. 19, 2018, printed as pp. 1/3-3/3. (Year: 2018).*
Xu et al. Selective inhibition of P-glycoprotein expression in mutidrug-resistant tumor cells by a designed transcriptional regulator. The Journal of Pharmacology and Experimental Therapeutics, vol. 302, No. 3, pp. 963-971, 2002. (Year: 2002).*
Berns et al. Repression of c-Myc responsive genes in cycling cells causes G1 arrest through reduction of cyclin E/CDK2 kinase activity. Oncogene, vol. 15, pp. 1347-1356, 1997. (Year: 1997).*
Bretones et al. Myc anc cell cycle control. Biochimica et Biophysica Acta, vol. 1849, pp. 506-516, 2015. (Year: 2015).*
Conti et al. Crystallographic analysis of the specific yet versatile recognition of distinct nuclear localization signals by karyopherin alpha. Structure, vol. 8, No. 3, pp. 329-338, Mar. 2000. (Year: 2000).*
Pengue et al. Repression of transcriptional activity at a distance by the evolutionarily conserved KRAB domain present in a subfamily of zinc finger proteins. Nucleic Acids Research, vol. 22, No. 15, pp. 2908-2914, 1994. (Year: 1994).*
Marampon et al. Down-regulation of c-Myc following MEK/ERK inhibition halts expression of malignant phenotype in rhabdomyosarcoma and in non muscle-derived brain tumors. Molecular Cancer, vol. 5: 31, Aug. 9, 2006, printed as pp. 1/17-17/17. (Year: 2006).*
Ayer, D. E. et al., Mad Proteins Contain a Dominant Transcription Repression Domain, Mol. Cell. Biol., 16(10):5772-5781 (1996).
Beaulieu, M-E. et al., Intrinsic cell-penetrating activity propels Omomyc from proof of concept to viable anti-MYC therapy, Sci Transl. Med., 11(484):1-27 (2019).
Beroukhim, R. et al., The landscape of somatic copy-No. alteration across human cancers, Nature, (46)7283:899-905 (2010).
Cowlings, V. H. and Cole, M. D., Mechanism of transcriptional activation by the Myc oncoproteins, Seminars in Cancer Biology, 16(4):242-252 (2006).
Dang, C. V. et al., The c-Myc target gene network, Semin Cancer Biol., 16:253-64 (2006).
Dang, C. V., MYC, Metabolism, Cell Growth, and Tumorigenesis, Cold Spring Harbor Perspectives in Medicine, 3:a014217 (2013).
Felsher, D. W. and Bishop, J. M., Reversible tumorigenesis by MYC in hematopoietic lineages, Molecular Cell, 4:199-207 (1999).
Fiorentino, F. P. et al., Growth suppression by MYC inhibition in small cell lung cancer cells with TP53 and RB1 inactivation, Oncotarget, 7(21):31014-31028 (2016).
Fisher, T. L. and Blenis, J., Evidence for Two Catalytically Active Kinase Domains in pp90rsk, Mol. Cell. Biol., 16(3):1212-1219 (1996).
Frank, S. R. et al., MYC recruits the TIP60 histone acetyltransferase complex to chromatin, EMBO Rep., 4(6):575-580 (2003).
Gashler, A. L. et al., A Novel Repression Module, an Extensive Activation Domain, and a Bipartite Nuclear Localization Signal Defined in the Immediate-Early Transcription Factor Egr-1, Mol. Cell Biol., 13(8):4556-4571 (1993).
Jennings, B. H. and Ish-Horowicz, The Groucho/TLE/Grg family of transcriptional co-repressors, Genome Biol., 9(1):205 (2008).

(Continued)

*Primary Examiner* — Jennifer Dunston
(74) *Attorney, Agent, or Firm* — Choate, Hall & Stewart LLP; Stephanie L. Schonewald; Mandeep Kaur

(57) ABSTRACT

The present disclosure provides technologies for MYC inhibition, including, e.g. MYC fusion polypeptides and compositions comprising the same as well as methods of using the same. In particular, the present disclosure, among others, provides fusion polypeptides comprising a mutant MYC polypeptide and a repressor domain. In some embodiments, such fusion polypeptides and compositions comprising the same can be useful for inducing cancer cell apoptosis. Accordingly, in some embodiments, such fusion polypeptides and compositions comprising the same can be useful for cancer treatment.

21 Claims, 2 Drawing Sheets

Specification includes a Sequence Listing.

(56) References Cited

OTHER PUBLICATIONS

Jung, L. A., et al., OmoMYC blunts promoter invasion by oncogenic MYC to inhibit gene expression characteristic of MYC-dependent tumors, Oncogene, 36(14):1911-1924 (2017).

Kalkat, M. et al., MYC Deregulation in Primary Human Cancers, Genes, 8:151 (2017).

Konermann, S. et al., Genome-scale transcriptional activation by an engineered CRISPR-Cas9 complex, Nature, 517(7536):583-588 (2014).

Lin, H., Capturing the cloud: UAP56 in nuage assembly and function, Cell, 151:699-701 (2012).

Loo, S. and Rine, J., Silencing and heritable domains of gene expression, Annu Rev Cell Dev Biol., 11:519-48 (1995).

Margolin, J. F. et al., Krüppel-associated boxes are potent transcriptional repression domains, PNAS, 91:4509-4513 (1994).

Nair, S. and Burley, S. K., X-ray structures of Myc-Max and Mad-Max recognizing DNA. Molecular bases of regulation by proto-oncogenic transcription factors, Cell, 112:193-205 (2003).

Savino, M. et al., The action mechanism of the Myc inhibitor termed Omomyc may give clues on how to target Myc for cancer therapy, Plos One 6(7):e22284 (2011).

Shi, Y. et al., Transcriptional repression by YY1, a human GLI-Krüppel-related protein, and relief of repression by adenovirus E1A protein, Cell, 67(2):377-88 (1991).

Smith, L. G. et al., The tangled-1 mutation alters cell division orientations throughout maize leaf development without altering leaf shape, Development, 122:481-9 (1996).

Soucek, L. et al., Design and properties of a Myc derivative that efficiently homodimerizes, Oncogene, 17:2463-2472 (1998).

Soucek, L. et al., Inhibition of Myc family proteins eradicates KRas-driven lung cancer in mice, Genes Dev., 27:504-513 (2013).

Soucek, L. et al., Modelling Myc inhibition as a cancer therapy, Nature, 455(7213):679-683 (2008).

Soucek, L. et al., Omomyc, a potential Myc dominant negative, enhances Myc-induced apoptosis, Cancer Research, 62(12):3507-10 (2002).

Thiel, G. et al., Biological activity and modular structure of RE-1-silencing transcription factor (REST), a repressor of neuronal genes, J. Biol. Chem., 273(41):26891-9 (1998).

Thiel, G. et al., Biological activity of mammalian transcriptional repressors, Biol. Chem., 382(6):891-902 (2001).

Wanzel, M. et al., Transcriptional repression by Myc, Trends in Cell Biology, 13(3):146-150 (2003).

Bellefroid, E. J. et al., The evolutionarily conserved Kruppel-associated box domain defines a subfamily of eukaryotic multifingered proteins, Proc. Natl. Acad. Sci., 88:3608-3612 (1991).

Liano-Pons, J. et al., The Multiple Faces of MNT and Its Role as a MYC Modulator, Cancers, 13:1-16 (2021).

\* cited by examiner

MUTANT MYC FUSION POLYPEPTIDES AND USES THEREOF

CROSS-REFERENCE TO RELATED APPLICATIONS

This application claims the benefit of U.S. Provisional Application No. 62/902,526 filed Sep. 19, 2019, the contents of which are hereby incorporated herein in their entirety.

SEQUENCE LISTING

The instant application contains a Sequence Listing which has been submitted electronically in ASCII format and is hereby incorporated by reference in its entirety. Said ASCII copy, created on Dec. 4, 2020, is named 2012611-0022_SL.txt and is 76,761 bytes in size.

BACKGROUND

Recent progress in the field of cancer research has identified a number of genes that are upregulated in malignant tumors as potential targets for therapeutics. However, many potential treatment targets have few to no therapeutically effective inhibitors. Existing inhibitor treatments may suffer from lack of selectivity and/or efficacy. These approaches therefore suffer from significant technological limitations.

SUMMARY

The present disclosure provides technologies for modulating (e.g., inhibiting) expression (e.g., level and/or activity) of MYC. Among other things, the present disclosure provides an insight that the inhibitory effect of a mutant MYC polypeptide (e.g., ones as described herein) can be modulated by fusing such a mutant MYC polypeptide to a regulatory domain. Among other things, the present inventors have demonstrated that fusing a regulatory domain (e.g., a repressor domain) to a mutant MYC polypeptide (e.g., a mutant MYC polypeptide that can competitively block MYC: MAX binding to E boxes) can amplify the inhibitory effect of such a mutant MYC polypeptide on expression (e.g., level and/or activity) of MYC.

In addition, the present disclosure, among others, recognizes that fusion polypeptides comprising a regulatory domain (e.g., a repressor domain) and a mutant MYC polypeptide can be more effective in killing and/or slowing growth of cancer cells, as compared to a mutant MYC polypeptide without such a regulatory domain (e.g., a repressor domain). Accordingly, the present disclosure also provides technologies for killing cancer cells and/or inducing cancer cell apoptosis. In some embodiments, such technologies can be useful for cancer treatment.

Some aspects provided herein relate to fusion polypeptides for MYC modulation (e.g., by reducing or inhibiting MYC expression). In some embodiments, such a fusion polypeptide comprises a mutant MYC and a repressor domain.

In some embodiments, a repressor domain included in a fusion polypeptide described herein is or comprises an eukaryotic polypeptide domain that can downregulate or silence transcription of a target gene. In some embodiments involving a fusion polypeptide described herein, a repressor domain is or comprises a transcriptional repressor domain and/or a histone deacetylase. In some embodiments involving such a fusion polypeptide described herein, a repressor domain is or comprises a Krüppel-associated box (KRAB) repressor domain, a mSIN interaction domain (SID), an RE1-silencing transcription factor (REST) repression domain, a thyroid hormone receptor repression domain, an Egr-1 repression domain, a transcriptional repressor protein YY1, a hairy protein family repression motif, an engrailed homology-1 repression motif, a human transducin-like Enhancer of split (TLE) protein, a histone deacetylase 2, a Silent Information Regulator 2 (Sir2), or combinations thereof. In some embodiments, a repressor domain included in a fusion polypeptide described herein can be or comprise a Krüppel-associated box (KRAB) repressor domain.

In some embodiments, a mutant MYC included in a fusion polypeptide described herein is or comprises a mutant of a wild-type MYC polypeptide or variants thereof. For example, in some embodiments, such a mutant MYC is or comprises a wild-type MYC polypeptide having at least one or more mutation(s). In some embodiments, such a mutant MYC is or comprises a dominant negative MYC polypeptide. An exemplary dominant negative MYC polypeptide may include, but is not limited to an Omomyc polypeptide. In some embodiments, such a mutant MYC polypeptide is or comprises a truncated MYC polypeptide that does not comprise a transactivation domain of MYC polypeptide. In some embodiments, such a mutant MYC is a C-terminus domain of MYC polypeptide. In some embodiments, such a mutant MYC is a mutant C-terminus domain of MYC polypeptide.

In some embodiments involving a fusion polypeptide described herein, a linker may be present to link a mutant MYC and a repressor domain included in such a fusion polypeptide. In some embodiments, peptidyl linkers may be used. One of ordinary skill in the art will recognize that linkers that are known for use in fusion polypeptides may be used in accordance with the present disclosure.

In some embodiments, a fusion polypeptide described herein can comprise an additional functional domain. Exemplary such a functional domain may be or comprise a repressor domain, a nuclear localization signal domain, a cell penetrating peptide, a detectable or secretion label, a protein-protein interaction domain, and combinations thereof. In some embodiments, an additional functional domain of a fusion polypeptide described herein is or comprises a nuclear localization signal domain of MYC. In some embodiments, an additional functional domain of a fusion polypeptide described herein is or comprises a nuclear localization signal domain of MYC. In some embodiments, an additional functional domain that can be included in a fusion polypeptide is or comprises a second repressor domain. Such a second repressor domain can be same as or different from the repressor domain that is already included in a fusion polypeptide.

In some embodiments, a mutant MYC and a repressor domain may be arranged in a fusion polypeptide described herein such that the mutant MYC is 5' of the repressor domain. In some embodiments, a mutant MYC and a repressor domain may be arranged in a fusion polypeptide described herein such that the mutant MYC is 3' of the repressor domain.

Components and/or compositions for making fusion polypeptides in accordance with the present disclosure are also provided herein. Accordingly, another aspect provided herein relates to a polynucleotide comprising a nucleic acid sequence that encodes a fusion polypeptide according to any one of the embodiments described herein. For example, in some embodiments, such a polynucleotide is a RNA polynucleotide comprising a nucleic acid sequence that encodes a fusion polypeptide described herein. In some embodiments, such a polynucleotide is a DNA polynucleotide comprising a nucleic acid sequence that encodes a fusion polypeptide described herein. In some embodiments, provided polynucleotides may be delivered by an expression vector and/or a viral particle. Accordingly, some aspects provided herein relate to a composition comprising a polynucleotide comprising a nucleic acid sequence that encodes a fusion polypeptide according to any one of the embodiments described herein. In some such embodiments, a composition may comprise an expression vector and/or other delivery vehicle (e.g., a viral particle).

Another aspect provided herein relates to a cell comprising one or more embodiments of a fusion polypeptide, polynucleotide, or composition comprising the same. In some embodiments, a cell may be a cancer cell.

In some embodiments, provided fusion polypeptides, polynucleotides, and/or compositions (e.g., ones described herein) can be included in pharmaceutical compositions, e.g., for use in inhibiting and/or reducing expression (e.g., activity and/or level) of MYC and/or for killing cancer cell and/or slowing cancer cell growth. Accordingly, another aspect provided herein relates to a pharmaceutical composition that delivers one or more embodiments of a fusion polypeptide, polynucleotide, and/or composition as described herein, which may optionally comprise a pharmaceutically acceptable excipient.

Another aspect provided herein relates to cells comprising a fusion polypeptide, polynucleotide and/or composition according to any one of the embodiments described herein. An exemplary cell may include, but is not limited to, a cancer cell.

Methods for using any embodiments of fusion polypeptides, polynucleotides, compositions (including, e.g. pharmaceutical compositions), and/or cells are also provided herein. In some embodiments, a method comprises: (a) contacting a target cell with a polynucleotide sequence that encodes a fusion polypeptide according to any of the embodiments herein or a composition comprising such a polynucleotide sequence; and/or (b) contacting a target cell with a fusion polypeptide according to any of the embodiments herein or a composition comprising such a fusion polypeptide. In some embodiments, a polynucleotide sequence can be or comprise any nucleic acid sequence that encodes one or more fusion polypeptides as described herein. In some embodiments, a target cell is or comprises a cancer cell.

Also within the scope of the present disclosure relates to methods of making fusion polypeptides and/or polynucleotides encoding the same as well as compositions and/or cells comprising the same. In some embodiments, provided herein is a method of making comprising recombinantly joining a mutant MYC-encoding nucleic acid and a repressor-encoding nucleic acid to form a polynucleotide comprising the mutant MYC-encoding nucleic acid and the repressor-encoding nucleic acid. In some embodiments, such a method further comprises expressing a recombinant polynucleotide (comprising a mutant MYC-encoding nucleic acid and a repressor-encoding nucleic acid) in a cell to produce a fusion polypeptide encoded by such a recombinant polynucleotide.

These and other aspects encompassed by the present disclosure, are described in more detail below and in the claims.

BRIEF DESCRIPTION OF THE DRAWINGS

FIG. 1A shows GFP expression at 72 hours post-transfection, while FIG. 1B shows GFP expression at 120 hours post-transfection.

CERTAIN DEFINITIONS

Figure 1A:
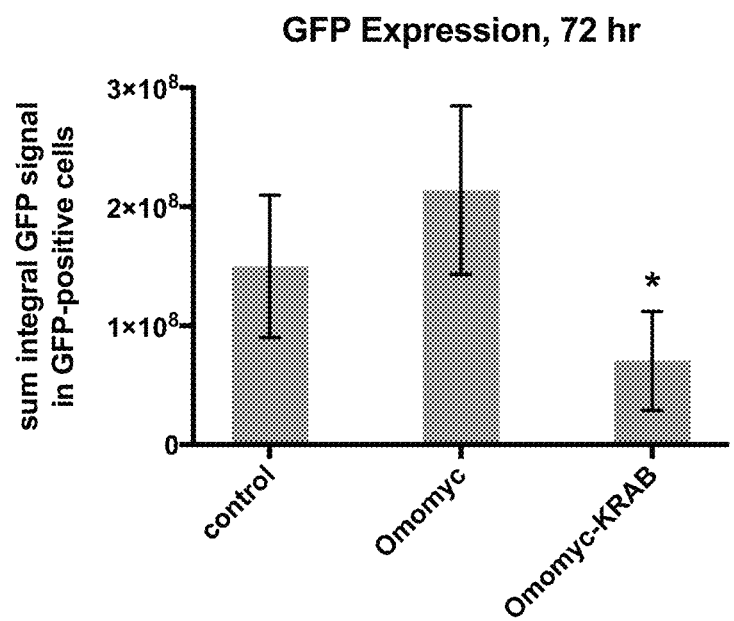
FIGS. 1A-1B depicts expression of a GFP target when a plasmid encoding either no polypeptide (control), a polypeptide containing mutant MYC (Omomyc), or a fusion polypeptide containing mutant MYC and a repressor domain (Omomyc-KRAB) is transfected into cells. Reduced sum integral GFP signal (y-axis) relative to the control indicates repression of GFP expression by the polypeptide.

Administering: As used herein, the term "administering" or "administration" typically refers to administration of a composition to a subject to achieve delivery of an agent that is, or is included in, the composition. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e.g., intrahepatic), mucosal, nasal, oral, rectal, subcutaneous, sublingual, topical, tracheal (e.g., by intratracheal instillation), vaginal, vitreal, etc. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Combination therapy: As used herein, the term "combination therapy" refers to those situations in which a subject is simultaneously exposed to two or more therapeutic regimens (e.g., two or more therapeutic agents). In some embodiments, two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition.

Comparable: As used herein, the term "comparable" refers to two or more agents, entities, situations, sets of conditions, subjects, etc., that may not be identical to one another but that are sufficiently similar to permit comparison therebetween so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Decrease, reduced, increased: As used herein, these terms or grammatically comparable comparative terms, indicate values that are relative to a comparable reference measurement. For example, in some embodiments, an assessed value or property achieved with an agent (e.g., fusion polypeptide or polynucleotide encoding the same) may be "decreased" relative to that obtained with a comparable reference agent (e.g., individual components of a fusion polypeptide or polynucleotide encoding individual components. Alternatively or additionally, in some embodiments, an assessed value or property achieved in a subject may be "increased" relative to that obtained in the same subject under different conditions (e.g., prior to or after an event; or presence or absence of an event such as administration of a fusion polypeptide, polynucleotide, or composition as described herein), or in a different, comparable subject (e.g., in a comparable subject that differs from the subject of interest in prior exposure to a condition, e.g., absence of administration of a fusion polypeptide, polynucleotide, or composition as described herein, etc.). In some embodiments, comparative terms refer to statistically relevant differences (e.g., that are of a prevalence and/or magnitude sufficient to achieve statistical relevance). Those skilled in the art will be aware, or will readily be able to determine, in a given context, a degree and/or prevalence of difference that is required or sufficient to achieve such statistical significance.

Delivery/contacting: As used interchangeably herein, the term "delivery," "delivering," or "contacting" refers to introduction of an agent (e.g., a fusion polypeptide, polynucleotide, or composition as described herein) into a target cell (e.g., cytosol of a target cell). A target cell can be cultured in vitro or ex vivo or be present in a subject (in vivo). Methods of introducing an agent (e.g., a fusion polypeptide, polynucleotide, or composition as described herein) into a target cell can vary with in vitro, ex vivo, or in vivo applications. In some embodiments, an agent (e.g., a fusion polypeptide, polynucleotide, or composition as described herein) can be introduced into a target cell in a cell culture, for example, by in vitro transfection (in the context of a polynucleotide). In some embodiments, an agent (e.g., a fusion polypeptide, polynucleotide, or composition as described herein) can be introduced into a target cell via delivery vehicles (e.g., nanoparticles, liposomes, and/or complexation with a cell-penetrating agent). In some embodiments, an agent (e.g., a fusion polypeptide, polynucleotide, or composition as described herein) can be introduced into a target cell in a subject by administering such an agent to a subject.

Dominant negative: As used herein, a "dominant negative" polypeptide is an inactive variant of a protein or polypeptide (e.g., a mutant MYC), which, by interacting with the cellular machinery, displaces an active protein from its interaction with the cellular machinery and/or competes with the active protein, thereby reducing the effect of the active protein. For example, a dominant negative receptor which binds a ligand, but does not transmit a signal in response to binding of the ligand, can reduce the biological effect of expression of the ligand. Likewise, a dominant negative catalytically-inactive kinase which interacts normally with one or more target proteins, but does not phosphorylate the target proteins, can reduce phosphorylation of the target proteins in response to a cellular signal. Similarly, a dominant negative transcription factor which binds to a promoter site in the control region of a gene, but does not increase gene transcription, can reduce the effect of a normal transcription factor, by occupying promoter binding sites without increasing transcription.

Inhibit: The term "inhibit" or "inhibition" in the context of MYC expression (e.g., activity and/or level) is not limited to only total inhibition. Thus, in some embodiments, partial inhibition or relative reduction is included within the scope of the term "inhibition." In some embodiments, the term refers to a reduction of MYC expression (e.g., activity and/or level) to a level that is reproducibly and/or statistically significantly lower than an initial or other appropriate reference level, which may, for example, be a baseline level of MYC expression (e.g., activity and/or level) in the absence or prior to administration of a fusion polypeptide, polynucleotide, and/or composition described herein. In some embodiments, the term refers to a reduction of MYC expression (e.g., activity and/or level) to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of MYC expression (e.g., activity and/or level) in the absence or prior to administration of a fusion polypeptide, polynucleotide, and/or composition described herein.

Mutant: As used herein, the term "mutant" refers to an organism, a cell, or a biomolecule (e.g., a nucleic acid or a protein) that comprises a genetic variation as compared to a reference organism, cell, or biomolecule. For example, a mutant nucleic acid may, in some embodiments, comprise a mutation, e.g., a nucleobase substitution, a deletion of one or more nucleobases, an insertion of one or more nucleobases, an inversion of two or more nucleobases, as, or a truncation, as compared to a reference nucleic acid molecule. Similarly, a mutant protein may comprise an amino acid substitution, insertion, inversion, or truncation, as compared to a reference polypeptide. Additional mutations, e.g., fusions and indels, are known to those of skill in the art. An organism or cell comprising or expressing a mutant nucleic acid or polypeptide is also sometimes referred to herein as a "mutant." In some embodiments, a mutant comprises a genetic variant that is associated with a loss of function of a gene product. A loss of function may be a complete abolishment of function, e.g., an abolishment of the enzymatic activity of an enzyme, or a partial loss of function, e.g., a diminished enzymatic activity of an enzyme. In some embodiments, a mutant comprises a genetic variant that is associated with a gain of function, e.g., with a negative or undesirable alteration in a characteristic or activity in a gene product. In some embodiments, a mutant is characterized by a reduction or loss in a desirable level or activity as compared to a reference; in some embodiments, a mutant is characterized by an increase or gain of an undesirable level or activity as compared to a reference. In some embodiments, a reference organism, cell, or biomolecule is a wild-type organism, cell, or biomolecule.

Nucleic acid/polynucleotide: As used herein, the terms "nucleic acid" and "polynucleotide" are used interchangeably, and refer to a polymer of at least 3 nucleotides or more. In some embodiments, a nucleic acid comprises DNA. In some embodiments, a nucleic acid comprises RNA. In some embodiments, a nucleic acid is single stranded. In some embodiments, a nucleic acid is double stranded. In some embodiments, a nucleic acid comprises both single and double stranded portions. In some embodiments, a nucleic acid comprises a backbone that comprises one or more phosphodiester linkages. In some embodiments, a nucleic acid comprises a backbone that comprises both phosphodiester and non-phosphodiester linkages. For example, in some embodiments, a nucleic acid may comprise a backbone that comprises one or more phosphorothioate or 5'-N-phosphoramidite linkages and/or one or more peptide bonds, e.g., as in a "peptide nucleic acid". In some embodiments, a nucleic acid comprises one or more, or all, natural residues (e.g., adenine, cytosine, deoxyadenosine, deoxycytidine, deoxyguanosine, deoxythymidine, guanine, thymine, uracil). In some embodiments, a nucleic acid comprises on or more, or all, non-natural residues. In some embodiments, a non-natural residue comprises a nucleoside analog (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 6-O-methylguanine, 2-thiocytidine, methylated bases, intercalated bases, and combinations thereof). In some embodiments, a non-natural residue comprises one or more modified sugars (e.g., 2'-fluororibose, ribose, 2'-deoxyribose, arabinose, and hexose) as compared to those in natural residues. In some embodiments, a nucleic acid has a nucleotide sequence that encodes a functional gene product such as an RNA or polypeptide. In some embodiments, a nucleic acid has a nucleotide sequence that comprises one or more introns. In some embodiments, a nucleic acid may be prepared by isolation from a natural source, enzymatic synthesis (e.g., by polymerization based on a complementary template, e.g., in vivo or in vitro, reproduction in a recombinant cell or system, or chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, or 20,000 or more residues or nucleotides long.

Polypeptide: The term "polypeptide", as used herein, generally has its art-recognized meaning of a polymer of at least three amino acids or more. Those of ordinary skill in the art will appreciate that the term "polypeptide" is intended to be sufficiently general as to encompass not only polypeptides having a complete sequence recited herein, but also to encompass polypeptides that represent functional, biologically active, or characteristic fragments, portions or domains (e.g., fragments, portions, or domains retaining at least one activity) of such complete polypeptides. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, polypeptides may comprise natural amino acids, non-natural amino acids, synthetic amino acids, and combinations thereof.

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control. In some embodiments, a reference is a negative control reference; in some embodiments, a reference is a positive control reference.

Subject: As used herein, the term "subject" refers an organism, typically a mammal (e.g., a human). In some embodiments, a subject is suffering from a disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered. In some embodiments, a subject is an individual suffering from cancer.

Variant: As used herein, the term "variant" refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. For example, a variant polypeptide may differ from a reference polypeptide as a result of one or more differences in amino acid sequence and/or one or more differences in chemical moieties (e.g., carbohydrates, lipids, etc.) covalently attached to the polypeptide backbone. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide.

Vector: As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked.

Standard techniques may be used for recombinant DNA, oligonucleotide synthesis, e.g., mRNA synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., Molecular Cloning: A Laboratory Manual (2nd ed., Cold Spring Harbor Laboratory Press, Cold Spring Harbor, N.Y. (1989)), which is incorporated herein by reference for any purpose.

DETAILED DESCRIPTION OF CERTAIN EMBODIMENTS

The present disclosure provides technologies for modulating (e.g., inhibiting) expression (e.g., level and/or activity) of MYC. The present disclosure, among other things, recognizes that when some or all of the dominant negative effect of Omomyc on MYC arises from it binding to E-boxes, then adding a repressor regulatory domain may amplify this effect. Thus, the present disclosure, among other things, provides an insight that the inhibitory effect of a mutant MYC polypeptide (e.g., ones as described herein) can be modulated by fusing such a mutant MYC polypeptide to a regulatory domain. The present disclosure also recognizes that such a repressor fusion strategy can lead to a stronger repression of MYC-activated promoters regardless of whether Omomyc:MYC or Omomyc:Omomyc is the dominant dimer species formed. Indeed, the present inventors have demonstrated that fusing a regulatory domain (e.g., a repressor domain) to a mutant MYC polypeptide (e.g., a mutant MYC polypeptide that can competitively block MYC:MAX binding to E boxes) can amplify the inhibitory effect of such a mutant MYC polypeptide on expression (e.g., level and/or activity) of MYC.

In addition, the present disclosure, among others, recognizes that fusion polypeptides comprising a regulatory domain (e.g., a repressor domain) and a mutant MYC polypeptide can be more effective in killing and/or slowing growth of cancer cells, as compared to a mutant MYC polypeptide without such a regulatory domain (e.g., a repressor domain). One of those skilled in the art, reading the present disclosure, will recognize that using an Omomyc-KRAB repressor fusion to kill cancer cells may be extended to fusions with other repressor domains (e.g., ones described herein). Accordingly, the present disclosure also provides technologies for killing cancer cells and/or inducing cancer cell apoptosis. In some embodiments, such technologies can be useful for cancer treatment.

A. MYC-Modulating Fusion Polypeptides

Some aspects provided herein relate to fusion polypeptides for MYC modulation (e.g., by reducing or inhibiting MYC expression). In some embodiments, such fusion polypeptides comprising a mutant MYC polypeptide can provide a greater reduction or inhibition of MYC expression (including, e.g., activity and/or level) by at least 30% or more, including, e.g., at least 40%, at least 50%, at least 60%, at least 70%, at least 80%, at least 90%, or more, as compared to that observed in the absence of such fusion polypeptides (e.g., a mutant MYC polypeptide alone). In some embodiments, such fusion polypeptides comprising a mutant MYC polypeptide can provide improved reduction and/or inhibition of MYC expression (including, e.g., activity and/or level) through fusion to one or more regulatory domains that modulate expression of a target gene. In some embodiments, a fusion polypeptide described herein comprises a mutant MYC and a repressor domain.

In some embodiments, a fusion polypeptide comprises a linker (e.g., ones described herein) between a mutant MYC (e.g., ones described herein) and a repressor domain (e.g., ones described herein).

In some embodiments, a mutant MYC and a repressor domain may be arranged in a fusion polypeptide described herein such that the mutant MYC is 5' of the repressor domain. In some embodiments, a mutant MYC and a repressor domain may be arranged in a fusion polypeptide described herein such that the mutant MYC is 3' of the repressor domain.

Exemplary Mutant MYC

The MYC gene is one of the most commonly dysregulated genes across all human cancers, and Myc expression often correlates with disease prognosis, metastatic potential, therapeutic resistance, and poor patient outcomes (Kalkat et al. (2017) *Genes (Basel)* 8: 151, which is incorporated by reference in its entirety). Myc deregulation can occur genetically, epigenetically, and post-transcriptionally through a wide variety of mechanisms. The widespread pleiotropic transcriptional changes induced by deregulated Myc act to potently transform cells to an oncogenic phenotype. Cancers with high levels of Myc have been experimentally shown to be correlated to its expression, such that inhibition of dysregulated Myc expression leads to rapid proliferative arrest and apoptosis of tumor cells (Felsher & Bishop (1999) Molecular Cell 4:199-207).

C-MYC is one of the most frequently amplified gene in human cancers (Beroukhim et al., Nature 2010). The human MYC oncogene protein family also includes the c-MYC paralogs N-MYC and L-MYC, which all function by forming a dimer with MAX through the common basic-region/ helix-loop-helix/leucine-zipper motif (Nair & Burley, Cell 2003). MYC:MAX heterodimers bind to E-box sequences (CACGTG) and activate transcription of the surrounding genes by recruiting histone acetyltransferases (Frank et al., EMBO Rep). MYC may regulate as much as 15% of all human genes (Dang et al. Semin Cancer Biol 2006), including many that are involved in cell cycle progression and proliferation. Interestingly, some data even suggest that pathologically high levels of MYC may also upregulate the expression of active genes without E-boxes in their promoters (Lin et al. Cell 2012).

In some embodiments, a fusion polypeptide comprises at least one or more (including, e.g., at least two, at least three, at least four, or more) mutant MYC. In some embodiments, at least two or more mutant MYC polypeptides in a fusion polypeptide described herein can be identical. In some embodiments, two or more different mutant MYC polypeptides may be used in a fusion polypeptide described herein.

In some embodiments, a mutant MYC of the present disclosure is or comprises a polypeptide that reduces or inhibits expression (e.g., level and/or activity) of MYC (e.g., m-Myc, N-Myc, and/or L-Myc). In some embodiments, a mutant MYC reduces or inhibits expression (e.g., level and/or activity) of MYC by at least 30% or more, including, e.g., at least 40%, at least 50%, at least 60%, at least 70%, at least 80%, at least 90%, or more, as compared to the expression and/or activity of Myc in the absence of such a mutant MYC.

In some embodiments, a mutant MYC included in a fusion polypeptide described herein is or comprises a mutant of a wild-type MYC polypeptide or variants thereof. For example, in some embodiments, such a mutant MYC is or comprises at least a portion of (including a full length of) a wild-type MYC polypeptide having at least one or more mutation(s), including, e.g., at least 2, at least 3, at least 4, at least 5, at least 6, at least 7, at least 8, at least 9, at least 10, at least 20, at least 30, at least 40, or more mutations. In some embodiments, a mutant MYC is within certain mutational distance (e.g., 80%, 90%, 95%, 96%, 97%, 98%, 99%) from a wild-type MYC.

In some embodiments, a mutant MYC included in a fusion polypeptide described herein is or comprises a mutant of a wild-type cMYC polypeptide or variants or homologs thereof. An exemplary amino acid sequence of a wild-type cMYC is shown below:

(SEQ ID NO: 1)
MPLNVSFTNRNYDLDYDSVQPYFYCDEEENFYQQQQQSELQPPAPSEDIW

KKFELLPTPPLSPSRRSGLCSPSYVAVTPFSLRGDNDGGGGSFSTADQLE

MVTELLGGDMVNQSFICDPDDETFIKNIIIQDCMWSGFSAAAKLVSEKLA

SYQAARKDSGSPNPARGHSVCSTSSLYLQDLSAAASECIDPSVVFPYPLN

DSSSPKSCASQDSSAFSPSSDSLLSSTESSPQGSPEPLVLHEETPPTTSS

DSEEEQEDEEEIDVVSVEKRQAPGKRSESGSPSAGGHSKPPHSPLVLKRC

HVSTHQHNYAAPPSTRKDYPAAKRVKLDSVRVLRQISNNRKCTSPRSSDT

EENVKRRTHNVLERQRRNELKRSFFALRDQIPELENNEKAPKVVILKKAT

AYILSVQAEEQKLISEEDLLRKRREQLKHKLEQLRNSCA, or a fragment thereof.

In some embodiments, a mutant MYC included in a fusion polypeptide described herein is or comprises a mutant of a wild-type N-MYC polypeptide or variants or homologs thereof. An exemplary amino acid sequence of a wild-type N-MYC is shown below:

(SEQ ID NO: 2)
MPSCSTSTMPGMICKNPDLEFDSLQPCFYPDEDDFYFGGPDSTPPGEDIW

KKFELLPTPPLSPSRGFAEHSSEPPSWVTEMLLENELWGSPAEEDAFGLG

-continued
GLGGLTPNPVILQDCMWSGFSAREKLERAVSEKLQHGRGPPTAGSTAQSP

GAGAASPAGRGHGGAAGAGRAGAALPAELAHPAAECVDPAVVFPFPVNKR

EPAPVPAAPASAPAAGPAVASGAGIAAPAGAPGVAPPRPGGRQTSGGDHK

ALSTSGEDTLSDSDDEDDEEEDEEEEIDVVTVEKRRSSSNTKAVTTFTIT

VRPKNAALGPGRAQSSELILKRCLPIHQQHNYAAPSPYVESEDAPPQKKI

KSEASPRPLKSVIPPKAKSLSPRNSDSEDSERRRNHNILERQRRNDLRSS

FLTLRDHVPELVKNEKAAKVVILKKATEYVHSLQAEEHQLLLEKEKLQAR

QQQLLKKIEHARTC, or a fragment thereof.

In some embodiments, a mutant MYC included in a fusion polypeptide described herein is or comprises a mutant of a wild-type L-MYC polypeptide or variants or homologs thereof. An exemplary amino acid sequence of a wild-type L-MYC is shown below:

(SEQ ID NO: 3)
MDYDSYQHYFYDYDCGEDFYRSTAPSEDIWKKFELVPSPPTSPPWGLGPG

AGDPAPGIGPPEPWPGGCTGDEAESRGHSKGWGRNYASIIRRDCMWSGFS

ARERLERAVSDRLAPGAPRGNPPKASAAPDCTPSLEAGNPAPAAPCPLGE

PKTQACSGSESPSDSENEEIDVVTVEKRQSLGIRKPVTITVRADPLDPCM

KHFHISIHQQQHNYAARFPPESCSQEEASERGPQEEVLERDAAGEKEDEE

DEEIVSPPPVESEAAQSCHPKPVSSDTEDVTKRKNHNFLERKRRNDLRSR

FLALRDQVPTLASCSKAPKVVILSKALEYLQALVGAEKRMATEKRQLRCR

QQQLQKRIAYLTGY, or a fragment thereof.

In some embodiments, a provided mutant MYC is or comprises a truncated MYC polypeptide that does not comprise a transactivation domain of MYC polypeptide. In some embodiments, a provided mutant MYC is a C-terminus domain of MYC polypeptide. In some embodiments, a provided mutant MYC is a mutant C-terminus domain of MYC polypeptide. In some embodiments, a provided mutant MYC is or comprises a variant of at least one domain of a Myc polypeptide, e.g., a basic helix-loop-helix DNA-binding domain, a leucine zipper domain, and a transactivation domain of a Myc polypeptide. A Myc polypeptide or transcription factor contains a basic helix-loop-helix DNA-binding domain, which enables it to bind to E-boxes throughout the genome to drive transcription of target genes, and a leucine zipper domain, enabling it to dimerize with other leucine zipper-containing transcription factor proteins (Cowling & Cole (2006) *Seminars in Cancer Biology* 16: 242-252). In order to bind E-boxes and drive transcription of target genes, Myc dimerizes with its obligate heterodimerization partner Max. Myc may also bind to Miz-1, and the Myc/Miz-1 heterodimer binds to non-E-box sequences to purportedly repress transcription (Wanzel et al. (2003) *Trends in Cell Biology* 13: 146-150, which is incorporated by reference in its entirety). Myc is often referred to as a "master transcriptional regulator" with greater than 10,000 binding sites throughout the human genome, and Myc coordinates a transcriptional regulatory network that consists of approximately 15% of all genes (Dang (2013) *Cold Spring Harbor Perspectives in Medicine* 3: pii: a014217, which is incorporated by reference in its entirety). The Myc target gene network is extremely large and diverse. Myc specifically controls gene expression programs responsible for cell proliferation, growth, metabolism, and evasion from apoptosis.

In some embodiments, a provided mutant MYC is or comprises a truncated MYC polypeptide, which may be or comprise one or more domains of a MYC polypeptide. For example, in some embodiments, such a truncated MYC polypeptide is or comprises a wild-type or variant of a leucine zipper domain of a Myc polypeptide. In some embodiments, such a truncated MYC polypeptide is or comprises a wild-type or a variant of a helix-loop-helix DNA-binding domain of a Myc polypeptide. In some embodiments, such a truncated MYC polypeptide is or comprises a wild-type or variant of a basic region of a Myc polypeptide. In some embodiments, such a truncated MYC polypeptide lacks a transactivation domain of a Myc polypeptide. In some embodiments, a truncated MYC polypeptide may comprise one or more domains from a C-terminal domain of a MYC polypeptide. An exemplary C-terminal domain of a MYC polypeptide includes a basic region, a helix-loop-helix DNA-binding domain, and a leucine zipper domain. In some embodiments, a truncated MYC polypeptide may comprise one or more mutant domains from a C-terminal domain of a MYC polypeptide, for example, a mutant domain with improved homodimerization and/or DNA binding capabilities. In some embodiments, a truncated MYC polypeptide may comprise one or more mutant domains from a C-terminal domain of a MYC polypeptide that can bind to E-box sequences either as a homodimer or as a heterodimer with MYC or MAX.

In some embodiments, a provided mutant MYC dimerizes with a Myc polypeptide (e.g., a wild-type Myc polypeptide), e.g., to inhibit Myc from dimerizing with its obligate heterodimerization partner Max.

In some embodiments, a provided mutant MYC dimerizes with a Max polypeptide (e.g., a wild-type Max polypeptide), e.g., to inhibit Myc from dimerizing with its obligate heterodimerization partner Max. In some embodiments, a dimer formed between a Myc inhibitor (e.g., a dominant negative variant of Myc) and Max can bind to an E-box sequence to form a complex that does not promote transcription.

In some embodiments, a provided mutant MYC does not interfere with Myc/Miz-1 dimerization and/or transcriptional repression.

In some embodiments, a provided mutant MYC is a dominant negative MYC. In some such embodiments, a dominant negative MYC can bind and sequester MYC, thereby preventing MYC from forming active MYC:MAX dimers. In some embodiments, a dominant negative MYC can form homodimers that can competitively block MYC:MAX binding to E-boxes (Jung et al., Oncogene 2017, which is incorporated by reference in its entirety). In some embodiments, such a dominant negative MYC is or comprises an Omomyc polypeptide. An Omomyc polypeptide is a mutant polypeptide derived from the basic helix-loop-helix and leucine zipper regions of a Myc polypeptide (Soucek et al. (1998) Oncogene 17: 1202199, which is incorporated by reference in its entirety). In some embodiments, an Omomyc lacks a N-terminus transactivation domain of a MYC polypeptide and carries four mutations (e.g., E63T, E70I, R77Q, R78N) in the leucine zipper domain that enable it to dimerize with c-MYC, N-MYC, and L-MYC (Fiorentino et al., Oncotarget 2016, which is incorporated by reference in its entirety). As the leucine zipper comprises the interface driving heterodimerization, these substitutions alter the protein's binding affinity for other leucine zipper-containing proteins. An Omomyc polypeptide is able to dimerize with wild type Myc. The affinity of Myc/Omomyc heterodimers for E-box sequences is greatly reduced compared to Myc/Max heterodimers. Thus, an Omomyc polypeptide sequesters Myc into nonfunctional complexes, preventing Myc from dimerizing with Max, from binding to DNA at E-boxes, and from driving gene expression, effectively acting as a dominant negative. Furthermore, an Omomyc polypeptide is able to dimerize with Max and bind to E-box sequences. However, because an Omomyc polypeptide lacks the Myc transactivation domain, these complexes are nonfunctional, thereby acting as a competitive inhibitor of Myc/Max heterodimers for binding to target genes. In some embodiments, an Omomyc polypeptide may enhance the repressive functions of Myc, for example by not interfering with Myc/Miz-1 dimerization and transcriptional repression (Savino et al. (2011) PLoS ONE 6: e22284, which is incorporated by reference in its entirety). In some embodiments, an Omomyc polypeptide acts as an edge-specific perturbation of a Myc network, selectively inhibiting Myc-mediated transcriptional activation while promoting Myc-mediated transcriptional repression. In some embodiments, an Omomyc polypeptide modulates a Myc transcriptome, e.g., modulating Myc activity towards repression, and/or switches Myc from a pro-oncogenic to a tumor suppressive role. In some embodiments, an Omomyc polypeptide enhances Myc-induced apoptosis in a manner dependent on Myc expression level, representing a powerful therapeutic strategy that specifically affects only Myc-deregulated cells (Soucek et al. (2002) Cancer Research 62: 3507-10, which is incorporated by reference in its entirety). Omomyc has been shown to have cancer-selective potency in in vivo models (Soucek et al., Nature 2008; Soucek et al., Genes Dev 2013; Beaulieu et al., Sci Transl Med 2019, each of which is incorporated by reference in its entirety).

In some embodiments, a provided mutant MYC is or comprises an amino acid sequence that is at least 70%, 75%, 80%, 85%, 90%, 91%, 92%, 93%, 94%, 95%, 96%, 97%, 98%, or 100% identical to the sequence set forth below:

```
                                       (SEQ ID NO: 4)
TEENVKRRTHNVLERQRRNELKRSFFALRDQIPELENNEKAPKVVILKKA

TAYILSVQAEEQKLISEEDLLRKRREQLKHKLEQLRNSCA,
``` or fragment thereof.

In some embodiments, a provided mutant MYC is or comprises an amino acid sequence that is at least 70%, 75%, 80%, 85%, 90%, 91%, 92%, 93%, 94%, 95%, 96%, 97%, 98%, or 100% identical to the sequence set forth below:

```
                                       (SEQ ID NO: 5)
SEDSERRRNHNILERQRRNDLRSSFLTLRDHVPELVKNEKAAKVVILKKA

TEYVHSLQAEEHQLLLEKEKLQARQQQLLKKIEHARTC,
``` or a fragment thereof.

In some embodiments, a provided mutant MYC is or comprises an amino acid sequence that is at least 70%, 75%, 80%, 85%, 90%, 91%, 92%, 93%, 94%, 95%, 96%, 97%, 98%, or 100% identical to the sequence set forth below:

```
                                       (SEQ ID NO: 6)
TEDVTKRKNHNFLERKRRNDLRSRFLALRDQVPTLASCSKAPKVVILSKA

LEYLQALVGAEKRMATEKRQLRCRQQQLQKRIAYLTGY,
``` or a fragment thereof.

In some embodiments, a provided mutant MYC is or comprises an amino acid sequence that is based on one of the sequences of SEQ ID NOs: 3-6 and includes 0-10 (e.g., 0, 1, 2, 3, 4, 5, 6, 7, 8, 9, 10) amino acid modifications to the respective sequences. Examples of amino acid modifications include, e.g., but not limited to replacement of amino acid side chains, substitution of amino acid residues, deletion of amino acid residues, and insertion of amino acid residues. In some embodiments, amino acid modification(s) are made to the sequences of SEQ ID NOs: 3-6 such that the resulting mutant MYC retains at least 70% or more (including, e.g., at least 80%, at least 90%, at least 95%, at least 98% or more) of the activity (e.g., reducing or inhibiting expression and/or activity of Myc itself or its interaction with heterodimerization partners), as compared to a reference MYC inhibitory agent (e.g., based on one of the sequences of SEQ ID NOs: 3-6 without amino acid modifications).

Exemplary Repressor Domains

At least one or more repressor domains, including, e.g., at least two, at least three, at least four, at least five or more repressor domains, are fused to one or more mutant MYC (e.g., ones described herein). In some embodiments, a repressor domain included in a fusion polypeptide described herein is or comprises an eukaryotic polypeptide domain that is capable of downregulating or silencing transcription of a target gene, e.g., whether via histone deacetylation, direct inhibition of general transcription factors, and/or other mechanisms that are not based simply on competitive bind to DNA. In some embodiments, a repressor domain is or comprises a DNA- or RNA-binding protein that inhibits or reduces expression of one or more genes by binding to an operator or associated silencer. In some embodiments, a repressor domain is or comprises a DNA-binding protein that blocks or reduces the attachment of RNA polymerase to a promoter, thus preventing transcription of one or more target genes into messenger RNA. In some embodiments, a repressor domain is or comprises an RNA-binding protein that binds to an mRNA and prevents translation of the mRNA into protein.

In some embodiments, a repressor domain is or comprises a transcriptional repressor domain and/or a histone deacetylase. In some embodiments, a repressor domain is or comprises a Krüppel-associated box (KRAB) repressor domain, mSIN interaction domain (SID), an RE1-silencing transcription factor (REST) repression domain, a thyroid hormone receptor repression domain, an Egr-1 repression domain, a transcriptional repressor protein YY1, a hairy protein family repression motif, an engrailed homology-1 repression motif, a human transducin-like Enhancer of split (TLE) protein, a histone deacetylase 2, a Silent Information Regulator 2 (Sir2), or combinations thereof.

In some embodiments, a repressor domain included in a fusion polypeptide described herein can be or comprise a Krüppel-associated box (KRAB) repressor domain, for example, of a KOX1 zinc finger protein (e.g., as described in Margolin et al., PNAS 1994, which is incorporated herein by reference in its entirety). In some embodiments, such a KRAB repressor domain is or comprises an amino acid sequence that is at least 70%, 75%, 80%, 85%, 90%, 91%, 92%, 93%, 94%, 95%, 96%, 97%, 98%, or 100% identical to the sequence set forth below:

(SEQ ID NO: 7)
MDAKSLTAWSRTLVTFKDVFVDFTREEWKLLDTA

QQIVYRNVMLENYKNLVSLGYQLTKPDVILRLE

KGEEPWLVEREIHQETHPDSETAFEIKSSV, or a fragment thereof.

In some embodiments, a provided repressor domain included in a fusion polypeptide described herein can be or comprise a mSIN interaction domain (SID). In some embodiments, such a SID is or comprises an amino acid sequence that is at least 70%, 75%, 80%, 85%, 90%, 91%, 92%, 93%, 94%, 95%, 96%, 97%, 98%, or 100% identical to the sequence set forth below:

(SEQ ID NO: 8)
MNIQMLLEAADYLERREREAEHGYASMLP, or a fragment thereof.

In some embodiments, a provided repressor domain included in a fusion polypeptide described herein can be or comprise a SID4X repressor domain. In some embodiments, such a SID4X repressor domain is or comprises an amino acid sequence that is at least 70%, 75%, 80%, 85%, 90%, 91%, 92%, 93%, 94%, 95%, 96%, 97%, 98%, or 100% identical to the sequence set forth below:

(SEQ ID NO: 9)
MNIQMLLEAADYLERREREAEHGYASMLPGSGMNIQMLLEAADYLE

RREREAEHGYASMLPGSGMNIQMLLEAADYLERREREAEHGYASML

PGSGMNIQMLLEAADYLERREREAEHGYASMLP, or a fragment thereof.

In some embodiments, a provided repressor domain included in a fusion polypeptide described herein can be or comprise a REST repressor domain. In some embodiments, a REST repressor domain is or comprises an amino acid sequence that is at least 70%, 75%, 80%, 85%, 90%, 91%, 92%, 93%, 94%, 95%, 96%, 97%, 98%, or 100% identical to one of the sequences set forth below:

(SEQ ID NO: 10)
MATQVMGQSSGGGGLFTSSGNIGMALPNDMYD

LHDLSKAELAAPQLIMLANVALTGEVNGSCCD

YLVGEERQMAELMPVGDNNFSDSEEGEGLEES

ADIKGEPHGLENMELRSLELSVVEPQPVFEAS

GAPDIYSSNKDLPPETPGAEDKGK, or a fragment thereof; and (SEQ ID NO: 11)
QNTRENLTGINSTVEEPVSPMLPPSAVEEREA

VSKTALASPPATMAANESQEIDEDEGIHSHEG

SDLSDNMSEGSDDSGLHGARPVPQESSRKNAK

EALAVKAAKGDFVCIFCDRSFRKGKDYSKHLN

RHLVNVYYLEEAAQGQE, or a fragment thereof.

In some embodiments, a provided repressor domain included in a fusion polypeptide described herein can be or comprise a thyroid hormone receptor repressor domain. In some embodiments, a thyroid hormone receptor repressor domain is or comprises an amino acid sequence that is at least 70%, 75%, 80%, 85%, 90%, 91%, 92%, 93%, 94%, 95%, 96%, 97%, 98%, or 100% identical to one of the sequences set forth below:

```
                                              (SEQ ID NO: 12)
    MDLVLDDSKRVAKRKLIEQNRERRRKEEMIRS

LQQRPEPTPEEWDLIHIATEAHRSTNAQGSHW

KQRRKFLPDDIGQSPIVSMPDGDKVDLEAFSE

FTKIITPAITRVVDFAKKLPMFSELPCEDQII

LLKGCCMEIMSLRAAVRYDPESDTLTLSGEMA

VKREQLKNGGLGVVSDAIFELGKSLSAFNLDD

TEVALLQAVLLMSTDRSGLLCVDKIEKSQEAY

LLAFEHYVNHRKHNIPHFWPKLLMKEREVQSS

ILYKGAAAEGRPGGSLGVHPEGQQLLGMHVVQ,
```
or a fragment thereof and

```
                                              (SEQ ID NO: 13)
    CRFKKCIYVGMATDLVLDDSKRLAKRKLIEEN

REKRRREELQKSIGHKPEPTDEEWELIKTVTE

AHVATNAQGSHWKQKRKFLPEDIGQAPIVNAP

EGGKVDLEAFSHFTKIITPAITRVVDFAKKLP

MFCELPCEDQIILLKGCCMEIMSLRAAVRYDP

ESETLTLNGEMAVTRGQLKNGGLGVVSDAIFD

LGMSLSSFNLDDTEVALLQAVLLMSSDRPGLA

CVERIEKYQDSFLLAFEHYINYRKHHVTHFWP

KLLMKVTDLRMIGACHASRFLHMKVECPTELF

PPLFL.
```

In some embodiments, a provided repressor domain included in a fusion polypeptide described herein can be or comprise an Egr-1 repressor domain. In some embodiments, such an Egr-1 repressor domain is or comprises an amino acid sequence that is at least 70%, 75%, 80%, 85%, 90%, 91%, 92%, 93%, 94%, 95%, 96%, 97%, 98%, or 100% identical to the sequence set forth below:

```
                                              (SEQ ID NO: 14)
    FQGLENRTQQPSLTPLSTIKAFATQSGSQDLK

ALNTTYQSQLIKPSRMRKYPNRPSKTPPHERP

Y,
```
or a fragment thereof.

In some embodiments, a provided repressor domain included in a fusion polypeptide described herein can be or comprise a transcriptional repressor protein YY1. In some embodiments, such a transcriptional repressor protein YY1 is or comprises an amino acid sequence that is at least 70%, 75%, 80%, 85%, 90%, 91%, 92%, 93%, 94%, 95%, 96%, 97%, 98%, or 100% identical to the sequence set forth below:

```
                                              (SEQ ID NO: 15)
    MASGDTLYIATDGSEMPAEIVELHEIEVETIP

VETIETTVVGEEEEEDDDDEDGGGGDHGGGGG

HGHAGHHHHHHHHHHHPPMIALQPLVTDDPTQ

VHHHQEVILVQTREEVVGGDDSDGLRAEDGFE

DQILIPVPAPAGGDDDYIEQTLVTVAAAGKSG

GGGSSSSGGGRVKKGGGKKSGKKSYLSGGAGA

AGGGGADPGNKKWEQKQVQIKTLEGEFSVTMW

SSDEKKDIDHETVVEEQIIGENSPPDYSEYMT

GKKLPPGGIPGIDLSDPKQLAEFARMKPRKIK

EDDAPRTIACPHKGCTKMFRDNSAMRKHLHTH

GPRVHVCAECGKAFVESSKLKRHQLVHTGEKP

FQCTFEGCGKRFSLDFNLRTHVRIHTGDRPYV

CPFDGCNKKFAQSTNLKSHILTHAKAKNNQ,
```
or a fragment thereof.

In some embodiments, a provided repressor domain included in a fusion polypeptide described herein can be or comprise a hairy protein family repression motif. In some embodiments, such a hairy protein family repression motif is or comprises an amino acid sequence that is at least 70%, 75%, 80%, 85%, 90%, 91%, 92%, 93%, 94%, 95%, 96%, 97%, 98%, or 100% identical to one of the sequences set forth below:

```
                                              (SEQ ID NO: 16)
    GSASSHSSAGYESAPGSSSSCSYAPPSPANSSYEPMDIKPS

VIQRVPMEQQPLSLVIKKQIKEEEQPWRPW,
```
or a fragment thereof;

```
                                              (SEQ ID NO: 17)
    GGAAPPPGSAPCKLGSQAGEAAKVFGGFQVVPAPDGQFAFLIPNGA

FAHSGPVIPVYTSNSGTSVGPNAVSPSSGSSLTADSMWRPWRN,
```
or a fragment thereof;

```
                                              (SEQ ID NO: 19)
    GSSSSSSTYSSASSCSSISPVSSGYASD

NESLLQISSPGQVWRPW,
```
or a fragment thereof; and

```
                                              (SEQ ID NO: 20)
    WRPW.
```

In some embodiments, a provided repressor domain included in a fusion polypeptide described herein can be or comprise an Engrailed homology-1 repression motif. In some embodiments, such an Engrailed homology-1 repression motif is or comprises an amino acid sequence that is at least 70%, 75%, 80%, 85%, 90%, 91%, 92%, 93%, 94%, 95%, 96%, 97%, 98%, or 100% identical to one of the sequences set forth below:

```
                                              (SEQ ID NO: 21)
    RQQQAAAAAATAAMMLERANFLNCFNPA

AYPRIHEEIVQSRLRRSAANAVIPPPM,
```
or a fragment thereof; and (SEQ ID NO: 22)
HRALPFSIDNILSLDFGRRKKVS, or a fragment thereof.

In some embodiments, a provided repressor domain included in a fusion polypeptide described herein can be or comprise a human transducin-like Enhancer of split (TLE) protein. In some embodiments, such a TLE protein is or comprises an amino acid sequence that is at least 70%, 75%, 80%, 85%, 90%, 91%, 92%, 93%, 94%, 95%, 96%, 97%, 98%, or 100% identical to one of the sequences set forth below:

(SEQ ID NO: 23)
MFPQSRHPTPHQAAGQPPFKFTIPESLDRIKEEFQFLQAQYHSLKLECEKL

ASEKTEMQRHYVMYYEMSYGLNIEMHKQTEIAKRLNTICAQVIPFLSQEH

QQQVAQAVERAKQVTMAELNAIIGQQQLQAQHLSHGHGPPVPLTPHPSGL

QPPGIPPLGGSAGLLALSSALSGQSHLAIKDDKKHHDAEHHRDREPGTSN

SLLVPDSLRGTDKRRNGPEFSNDIKKRKVDDKDSSHYDSDGDKSDDNLVV

DVSNEDPSSPRASPAHSPRENGIDKNRLLKKDASSSPASTASSASSTSLK

SKEMSLHEKASTPVLKSSTPTPRSDMPTPGTSATPGLRPGLGKPPAIDPL

VNQAAAGLRTPLAVPGPYPAPFGMVPHAGMNGELTSPGAAYASLHNMSPQ

MSAAAAAAAVVAYGRSPMVGFDPPPHMRVPTIPPNLAGIPGGKPAYSFHV

TADGQMQPVPFPPDALIGPGIPRHARQINTLNHGEVVCAVTISNPTRHVY

TGGKGCVKVWDISHPGNKSPVSQLDCLNRDNYIRSCKLLPDGCTLIVGGE

ASTLSIWDLAAPTPRIKAELTSSAPACYALAISPDSKVCFSCCSDGNIAV

WDLHNQTLVRQFQGHTDGASCIDISNDGTKLWTGGLDNTVRSWDLREGRQ

LQQHDFTSQIFSLGYCPTGEWLAVGMESSNVEVLHVNKPDKYQLHLHESC

VLSLKFAYCGKWFVSTGKDNLLNAWRTPYGASIFQSKESSSVLSCDISVD

DKYIVTGSGDKKATVYEVIY, or a fragment thereof;

(SEQ ID NO: 24)
MYPQGRHPTPLQSGQPFKFSILEICDRIKEEFQFLQAQYHSLKLECEKLA

SEKTEMQRHYVMYYEMSYGLNIEMHKQAEIVKRLSGICAQIIPFLTQEHQ

QQVLQAVERAKQVTVGELNSLIGQQLQPLSHHAPPVPLTPRPAGLVGGSA

TGLLALSGALAAQAQLAAAVKEDRAGVEAEGSRVERAPSRSASPSPPESL

VEEERPSGPGGGKQRADEKEPSGPYESDEDKSDYNLVVDEDQPSEPPSP

ATTPCGKVPICIPARRDLVDSPASLASSLGSPLPRAKELILNDLPASTPA

SKSCDSSPPQDASTPGPSSASHLCQLAAKPAPSTDSVALRSPLTLSSPFT

TSFSLGSHSTLNGDLSVPSSYVSLHLSPQVSSSVVYGRSPVMAFESHPHL

RGSSVSSSLPSIPGGKPAYSFHVSADGQMQPVPFPSDALVGAGIPRHARQ

LHTLAHGEVVCAVTISGSTQHVYTGGKGCVKVWDVGQPGAKTPVAQLDCL

NRDNYIRSCKLLPDGRSLIVGGEASTLSIWDLAAPTPRIKAELTSSAPAC

YALAVSPDAKVCFSCCSDGNIVVWDLQNQTMVRQFQGHTDGASCIDISDY

GTRLWTGGLDNTVRCWDLREGRQLQQHDFSSQIFSLGHCPNQDWLAVGME

-continued
SSNVEILHVRKPEKYQLHLHESCVLSLKFASCGRWFVSTGKDNLLNAWRT

PYGASIFQSKESSSVLSCDISRNNKYIVTGSGDKKATVYEVVY.

or a fragment thereof;

(SEQ ID NO: 25)
MYPQGRHPAPHQPGQPGFKFTVAESCDRIKDEFQFLQAQYHSLKVEYDKL

ANEKTEMQRHYVMYYEMSYGLNIEMHKQTEIAKRLNTILAQIMPFLSQEH

QQQVAQAVERAKQVTMTELNAIIGQQQLQAQHLSHATHGPPVQLPPHPSG

LQPPGIPPVTGSSSGLLALGALGSQAHLTVKDEKNHHELDHRERESSANN

SVSPSESLRASEKHRGSADYSMEAKKRKAEEKDSLSRYDSDGDKSDDLVV

DVSNEDPATPRVSPAHSPPENGLDKARSLKKDAPTSPASVASSSSTPSSK

TKDLGHNDKSSTPGLKSNTPTPRNDAPTPGTSTTPGLRSMPGKPPGMDPI

GIMASALRTPISITSSYAAPFAMMSHHEMNGSLTSPGAYAGLHNIPPQMS

AAAAAAAAAYGRSPMVSFGAVGFDPHPPMRATGLPSSLASIPGGKPAYSF

HVSADGQMQPVPFPHDALAGPGIPRHARQINTLSHGEVVCAVTISNPTRH

VYTGGKGCVKIWDISQPGSKSPISQLDCLNRDNYIRSCKLLPDGRTLIVG

GEASTLTIWDLASPTPRIKAELTSSAPACYALAISPDAKVCFSCCSDGNI

AVWDLHNQTLVRQFQGHTDGASCIDISHDGTKLWTGGLDNTVRSWDLREG

RQLQQHDFTSQIFSLGYCPTGEWLAVGMESSNVEVLHHTKPDKYQLHLHE

SCVLSLKFAYCGKWFVSTGKDNLLNAWRTPYGASIFQSKESSSVLSCDIS

ADDKYIVTGSGDKKATVYEVIY, or a fragment thereof; and (SEQ ID NO: 26)
MIRDLSKMYPQTRHPAPHQPAQPFKFTISESCDRIKEEFQFLQAQYHSLK

LECEKLASEKTEMQRHYVMYYEMSYGLNIEMHKQAEIVKRLNAICAQVIP

FLSQEHQQQVVQAVERAKQVTMAELNAIIGQQLQAQHLSHGHGLPVPLTP

HPSGLQPPAIPPIGSSAGLLALSSALGGQSHLPIKDEKKHHDNDHQRDRD

SIKSSSVSPSASFRGAEKHRNSADYSSESKKQKTEEKEIAARYDSDGEKS

DDNLVVDVSNEDPSSPRGSPAHSPRENGLDKTRLLKKDAPISPASIASSS

STPSSKSKELSLNEKSTTPVSKSNTPTPRTDAPTPGSNSTPGLRPVPGKP

PGVDPLASSLRTPMAVPCPYPTPFGIVPHAGMNGELTSPGAAYAGLHNIS

PQMSAAAAAAAAAAYGRSPVVGFDPHHHMRVPAIPPNLTGIPGGKPAYS

FHVSADGQMQPVPFPPDALIGPGIPRHARQINTLNHGEVVCAVTISNPTR

HVYTGGKGCVKVWDISHPGNKSPVSQLDCLNRDNYIRSCRLLPDGRTLIV

GGEASTLSIWDLAAPTPRIKAELTSSAPACYALAISPDSKVCFSCCSDGN

IAVWDLHNQTLVRQFQGHTDGASCIDISNDGTKLWTGGLDNTVRSWDLRE

GRQLQQHDFTSQIFSLGYCPTGEWLAVGMENSNVEVLHVTKPDKYQLHLH

ESCVLSLKFAHCGKWFVSTGKDNLLNAWRTPYGASIFQSKESSSVLSCDI

SVDDKYIVTGSGDKKATVYEVIY, or a fragment thereof.

In some embodiments, a provided repressor domain included in a fusion polypeptide described herein can be or comprise a histone deacetylase 2 (HDAC2). In some embodiments, such a HDAC2 is or comprises an amino acid sequence that is at least 70%, 75%, 80%, 85%, 90%, 91%, 92%, 93%, 94%, 95%, 96%, 97%, 98%, or 100% identical to the sequence set forth below:

(SEQ ID NO: 27)
MAYSQGGGKKKVCYYYDGDIGNYYYGQGHPMKPHRIRMTHNLLLNYGLYR

KMEIYRPHKATAEEMTKYHSDEYIKFLRSIRPDNMSEYSKQMQRFNVGED

CPVFDGLFEFCQLSTGGSVAGAVKLNRQQTDMAVNWAGGLHHAKKSEASG

FCYVNDIVLAILELLKYHQRVLYIDIDIHHGDGVEEAFYTTDRVMTVSFH

KYGEYFPGTGDLRDIGAGKGKYYAVNFPMRDGIDDESYGQIFKPIISKVM

EMYQPSAVVLQCGADSLSGDRLGCFNLTVKGHAKCVEVVKTFNLPLLMLG

GGGYTIRNVARCWTYETAVALDCEIPNELPYNDYFEYFGPDFKLHISPSN

MTNQNTPEYMEKIKQRLFENLRMLPHAPGVQMQAIPEDAVHEDSGDEDGE

DPDKRISIRASDKRIACDEEFSDSEDEGEGGRRNVADHKKGAKKARIEED

KKETEDKKTDVKEEDKSKDNSGEKTDTKGTKSEQLSNP.

In some embodiments, a provided repressor domain included in a fusion polypeptide described herein can be or comprise a Silent Information Regulator 2 (Sir2) or sirtuin 1 (SIRT1). In some embodiments, such a Sir2 or SIRT1 is or comprises an amino acid sequence that is at least 70%, 75%, 80%, 85%, 90%, 91%, 92%, 93%, 94%, 95%, 96%, 97%, 98%, or 100% identical to the sequence set forth below:

(SEQ ID NO: 28)
MADEAALALQPGGSPSAAGADREAASSPAGEPLRKRPRRDGPGLERSPGE

PGGAAPEREVPAAARGCPGAAAAALWREAEAEAAAAGGEQEAQATAAAGE

GDNGPGLQGPSREPPLADNLYDEDDDDEGEEEEEAAAAAIGYRDNLLFGD

EIITNGFHSCESDEEDRASHASSSDWTPRPRIGPYTFVQQHLMIGTDPRT

ILKDLLPETIPPPELDDMTLWQIVINILSEPPKRKKRKDINTIEDAVKLL

QECKKIIVLTGAGVSVSCGIPDFRSRDGIYARLAVDFPDLPDPQAMFDIE

YFRKDPRPFFKFAKEIYPGQFQPSLCHKFIALSDKEGKLLRNYTQNIDTL

EQVAGIQRIIQCHGSFATASCLICKYKVDCEAVRGDIFNQVVPRCPRCPA

DEPLAIMKPEIVFFGENLPEQFHRAMKYDKDEVDLLIVIGSSLKVRPVAL

IPSSIPHEVPQILINREPLPHLHFDVELLGDCDVIINELCHRLGGEYAKL

CCNPVKLSEITEKPPRTQKELAYLSELPPTPLHVSEDSSSPERTSPPDSS

VIVTLLDQAAKSNDDLDVSESKGCMEEKPQEVQTSRNVESIAEQMENPDL

KNVGSSTGEKNERTSVAGTVRKCWPNRVAKEQISRRLDGNQYLFLPPNRY

IFHGAEVYSDSEDDVLSSSSCGSNSDSGTCQSPSLEEPMEDESEIEEFYN

GLEDEPDVPERAGGAGFGTDGDDQEAINEAISVKQEVTDMNYPSNKS.

Linkers

In some embodiments involving a fusion polypeptide described herein, a linker may be present to link a mutant MYC (e.g., ones described herein) and a repressor domain (e.g., ones described herein) included in such a fusion polypeptide. In some embodiments, peptidyl linkers may be used. One of ordinary skill in the art will recognize that linkers that are known for use in fusion polypeptides may be used in accordance with the present disclosure.

In some embodiments, a linker is or comprises one or more flexible glycine-serine linkers. For example, in some embodiments, an exemplary flexible glycine-serine linker is or comprises the amino acid sequence of (SEQ ID NO: 18)
SGGGSGGSGS.

In some embodiments, a linker is or comprises a native c-MYC linker. For example, in some embodiments, an exemplary c-MYC linker is or comprises an amino acid sequence from a wild-type MYC sequence. In some embodiments, a linker is or comprises an amino acid sequence found between a transactivation domain and a C-terminal domain of MYC, or a variant thereof. In some embodiments, a linker is or comprises an amino acid sequence found between a native nuclear localization signal domain and other domains of MYC, or a variant thereof.

In some embodiments, a linker is or comprises different arrangements of a sequence, such as glycine-serine linker sequence, for example different lengths or combinations as described in van Rosmalen et al., *Biochemistry* (2017) 56: 6565-6574, which is incorporated herein by reference in its entirety.

In some embodiments, a linker may have a length of at least 3 amino acids or more, including, e.g., at least 4 amino acids, at least 5 amino acids, at least 6 amino acids, at least 7 amino acids, at least 8 amino acids, at least 9 amino acids, at least 10 amino acids, at least 15 amino acids, at least 20 amino acids, or more.

Optional Additional Functional Domains

In some embodiments, a fusion polypeptide described herein can comprise at least one or more (including, e.g., at least two, at least three, at least four, at least five or more) additional functional domain(s). Exemplary such a functional domain may be or comprise a repressor domain, a nuclear localization signal domain, a cell penetrating peptide, a detectable or secretion label, a protein-protein interaction domain, and combinations thereof.

In some embodiments, at least one additional functional domain of a fusion polypeptide described herein is or comprises a nuclear localization signal domain of MYC. In some embodiments, such fusion can increase the toxicity of a mutant MYC included in a fusion polypeptide. In some embodiments, a C-terminal c-MYC nuclear localization signal domain can be added to a fusion polypeptide comprising a mutant MYC and a repressor domain. In some such embodiments, a mutant MYC (e.g., ones described herein such as Omomyc) may be located 5' of a repressor domain (e.g., ones described herein such as a KRAB repressor domain).

In some embodiments, an additional functional domain of a fusion polypeptide described herein is or comprises a cell penetrating peptide. A cell-penetrating (CPP) is or comprises a carrier peptide that is capable of crossing a biological membrane or a physiological barrier. In some embodiments, cell penetrating peptides are also called cell-permeable peptides, protein-transduction domains (PTD) or membrane translocation sequences (MTS). CPPs have the ability to translocate in vitro and/or in vivo the mammalian cell membranes and enter into cells and/or cell nuclei, and directs a fusion polypeptide described herein, to a desired cellular destination. In some embodiments, a CPP can direct or facilitate penetration of a fusion polypeptide described herein across a phospholipid, mitochondrial, endosomal or nuclear membrane. A CPP can also direct a fusion polypeptide described herein from outside the cell through the plasma membrane, and into the cytoplasm or cytosol or to a desired location within the cell, e.g., the nucleus, the mitochondria, the endoplasmic reticulum, a lysosome, or a peroxisome. Alternatively or in addition, a CPP can direct a fusion polypeptide across the blood-brain or hematoretinal, trans-mucosal, skin, gastrointestinal and/or pulmonary barriers. Several proteins and their peptide derivatives have been found to possess cell internalization properties including but not limited to the Human Immunodeficency Virus type 1 (HIV-1) protein Tat (Ruben et al. J. Virol. 63, 1-8 (1989)), the herpes virus tegument protein VP22 (Elliott and O'Hare, Cell 88, 223-233 (1997)), Penetratin (Derossi et al., J. Biol. Chern. 271, 18188-18193 (1996)), protegrin 1 (PG-1) anti-microbial peptide SynB (Kokryakov et al., FEBS Lett. 327, 231-236 (1993)) and the basic fibroblast growth factor (Jans, Faseb J. 8, 841-847 (1994)). These carrier peptides show little sequence homology with each other, but are all highly cationic and arginine or lysine rich. Indeed, synthetic poly-arginine peptides have been shown to be internalized with a high level of efficiency (Futaki et al., J. Mol. Recognit. 16, 260-264 (2003); Suzuki et al., J. Biol. Chem. (2001)). In some embodiments, a CPP that may be used in accordance with the present disclosure is or comprises a functional penetrating Phylomer peptide (FPPa). FPPa polypeptides as described in Wang et al., *Oncogene* (2019) 38: 140-150, which is incorporated herein by reference in its entirety, are well known in the art and can be used in accordance with the present disclosure.

In some embodiments, an additional functional domain of a fusion polypeptide described herein is or comprises a detectable or secretion label, for example human serum albumin signal peptide or the constant domain of IgG (Fc) as described in Carter et al. and Zhang et al., each of which is incorporated herein by reference in its entirety.

In some embodiments, an additional functional domain that can be included in a fusion polypeptide is or comprises a protein-protein interaction domain, e.g., which enhances the affinity and/or specificity of dimer formation.

In some embodiments, an additional functional domain that can be included in a fusion polypeptide is or comprises a second repressor domain (e.g., ones described herein). Such a second repressor domain can be same as or different from the repressor domain that is already included in a fusion polypeptide.

In some embodiments, a fusion polypeptide described herein includes a mutant MYC (e.g., a C-terminal domain of MYC) and a KRAB repressor domain of the KOX1 zinc finger protein (Margolin et al., PNAS 1994) with a flexible glycine-serine linker connecting the mutant MYC and the KRAB repressor domain. In some embodiments, such a fusion polypeptide is or comprises the amino acid sequence as set forth below:

(SEQ ID NO: 29)
MTEENVKRRTHNVLERQRRNELKRSFFALRDQIPELENNEKAPKVVILKK

ATAYILSVQAETQKLISEIDLLRKQNEQLKHKLEQLRNSCASGGGSGGSG

SMDAKSLTAWSRTLVTFKDVFVDFTREEWKLLDTAQQIVYRNVMLENYKN

LVSLGYQLTKPDVILRLEKGEEPWLVEREIHQETHPDSETAFEIKSSV

B. Polynucleotides Encoding MYC-Modulating Fusion Polypeptides

Components and/or compositions for making fusion polypeptides in accordance with the present disclosure are also provided herein. Accordingly, another aspect provided herein relates to a polynucleotide comprising a nucleic acid sequence that encodes a fusion polypeptide according to any one of the embodiments described herein. For example, in some embodiments, such a polynucleotide is an RNA polynucleotide comprising a nucleic acid sequence that encodes a fusion polypeptide described herein. In some embodiments, such an RNA polynucleotide is single stranded. In some embodiments, such an RNA polynucleotide is double stranded. In some embodiments, such an RNA polynucleotide comprises both single and double stranded portions. An RNA polynucleotide can be a regulatory RNA (e.g., siRNA, microRNA, etc.), or a messenger RNA (mRNA) polynucleotide.

In some embodiments, such a polynucleotide is a DNA polynucleotide comprising a nucleic acid sequence that encodes a fusion polypeptide described herein.

In some embodiments, a polynucleotide encodes a fusion polypeptide including a mutant MYC (e.g., a C-terminal domain of MYC) and a KRAB repressor domain of the KOX1 zinc finger protein (Margolin et al., PNAS 1994) with a flexible glycine-serine linker connecting the mutant MYC and the KRAB repressor domain. In some embodiments, such a polynucleotide is or comprises the nucleic acid sequence as described in Example 1 or 2.

In some embodiments, provided polynucleotides may be delivered by an expression vector or other delivery vehicle (e.g., a viral particle).

C. Methods of Making Fusion Peptides and/or Polynucleotides Described Herein

Also within the scope of the present disclosure relates to methods of making fusion polypeptides and/or polynucleotides encoding the same as well as compositions and/or cells comprising the same. In some embodiments, provided herein is a method of making comprising recombinantly joining a mutant MYC-encoding nucleic acid and a repressor-encoding nucleic acid to form a polynucleotide comprising the mutant MYC-encoding nucleic acid and the repressor-encoding nucleic acid. In some embodiments, such a method further comprises expressing a recombinant polynucleotide (that comprises a mutant MYC-encoding nucleic acid and a repressor-encoding nucleic acid) in a cell to produce a fusion polypeptide encoded by such a recombinant polynucleotide.

D. Compositions that Deliver a Fusion Polypeptide and/or Polynucleotide Encoding the Same In accordance with the present disclosure, any of a variety of modalities may be utilized to deliver a fusion polypeptide described herein and/or a polynucleotide encoding the same. To give but a few examples, in some embodiments, a fusion polypeptide described herein and/or a polynucleotide encoding the same is administered (i.e., to a subject or system). In some embodiments, a nucleic acid that encodes a fusion polypeptide may be administered; in some such embodiments, the encoding nucleic acid may be associated with one or more elements that directs its expression. In some embodiments, a cell containing and/or expressing a fusion polypeptide described herein and/or a polynucleotide encoding the same is administered; in some such embodiments, the cell is a cancer cell. In some embodiments, a viral particle containing a fusion polypeptide described herein and/or a polynucleotide encoding and/or expressing it is administered.

Thus in some embodiments, a fusion polypeptide described herein can be directly administered (e.g., as protein). As such, in some embodiments, a composition that delivers a fusion polypeptide described herein includes a fusion polypeptide described herein.

In some embodiments, a fusion polypeptide described herein can be delivered as a gene-encoded therapy (including, e.g., mRNA, DNA, viral vector). In some embodiments, a fusion polypeptide described herein can be delivered by delivering a nucleic acid that encodes a fusion polypeptide described herein, a vector that includes such a nucleic acid, a cell that includes a nucleic acid that encodes a fusion polypeptide described herein, a cell that includes a vector comprising a nucleic acid that encodes fusion polypeptide described herein, and/or a cell that includes a fusion polypeptide described herein. As such, in some embodiments, a composition that delivers a fusion polypeptide described herein includes a nucleic acid that encodes a fusion polypeptide described herein, a vector that includes such a nucleic acid, a cell that includes a nucleic acid that encodes a fusion polypeptide described herein, a cell that includes a vector comprising a nucleic acid that encodes a fusion polypeptide described herein, and/or a cell that includes a fusion polypeptide described herein.

In some embodiments, a fusion polypeptide described herein can be delivered by delivering a viral particle that comprises a nucleic acid that encodes a fusion polypeptide described herein, a vector that includes such a nucleic acid, and/or a fusion polypeptide described herein. As such, in some embodiments, a composition that delivers a fusion polypeptide described herein includes a viral particle that comprises a nucleic acid that encodes a fusion polypeptide described herein, a vector that includes such a nucleic acid, and/or a fusion polypeptide described herein.

Cells Comprising Fusions Polypeptides and/or Polynucleotides Described Herein

Another aspect provided herein relates to a cell comprising one or more embodiments of a fusion polypeptide described herein, a polynucleotide encoding a fusion polypeptide described herein, or a composition comprising the same.

Any cells can be chosen to express a fusion polypeptide and/or polynucleotide described herein. In some embodiments, cells to be contacted with any of fusion polypeptides, polynucleotides, and/or compositions described herein can be wild-type cells, normal cells, diseased cells (e.g., cancer cells), or transgenic cells. In some embodiments, cells to be contacted with any of fusion polypeptides, polynucleotides, and/or compositions described herein can be eukaryotic cells (e.g., mammalian cells).

In some embodiments, cells for use in accordance with the present disclosure are cancer cells. For example, cancer cells may be from leukemia, neuroblastoma, lymphoma, breast cancer, colon cancer, lung cancer, ovarian cancer, thymoma, germ cell tumor, myeloma, melanoma, rectal cancer, stomach cancer, pancreatic cancer, testicular cancer, skin cancer, sarcoma, or brain cancer.

Pharmaceutical Compositions

In some embodiments, a composition that delivers a fusion polypeptide and/or polynucleotide encoding the same can be a pharmaceutical composition. In some embodiments, provided fusion polypeptides, polynucleotides, and/or compositions (e.g., ones described herein) can be included in pharmaceutical compositions, for example, for use in selectively killing cancer cells and/or slowing or inhibiting cancer cell growth. Accordingly, another aspect provided herein relates to a pharmaceutical composition that delivers one or more embodiments of a fusion polypeptide, polynucleotide, and/or composition as described herein, which may optionally comprise a pharmaceutically acceptable excipient.

In some embodiments, a pharmaceutical composition can include a pharmaceutically acceptable carrier or excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro (Lippincott, Williams & Wilkins, Baltimore, MD, 2006; incorporated herein by reference) discloses various excipients used in formulating pharmaceutical compositions and known techniques for the preparation thereof. Suitable pharmaceutically acceptable carriers include but are not limited to water, salt solutions (e.g., NaCl), saline, buffered saline, glycerol, sugars such as mannitol, sucrose, or others, dextrose, fatty acid esters, etc., as well as combinations thereof.

A pharmaceutical composition can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like), which do not deleteriously react with the active compounds or interfere with their activity. In certain embodiments, a water-soluble carrier suitable for intravenous administration is used. In some embodiments, a pharmaceutical composition can be sterile.

A suitable pharmaceutical composition, if desired, can also contain minor amounts of wetting or emulsifying agents, or pH buffering agents. A pharmaceutical composition can be a liquid solution, suspension, or emulsion.

A pharmaceutical composition can be formulated in accordance with the routine procedures as a pharmaceutical composition adapted for administration to human beings. The formulation of a pharmaceutical composition should suit the mode of administration. For example, in some embodiments, a composition for intravenous administration is typically a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where a pharmaceutical composition is to be administered by infusion, it can be dispensed with an infusion bottle containing sterile pharmaceutical grade water, saline or dextrose/water. Where a pharmaceutical composition is administered by injection, an ampule of sterile water for injection or saline can be provided so that the ingredients may be mixed prior to administration.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts or cells in vitro or ex vivo. Modification of pharmaceutical compositions suitable for administration to humans in order to render the compositions suitable for administration to various animals or cells in vitro or ex vivo is well understood, and the ordinarily skilled practitioner, e.g., a veterinary pharmacologist, can design and/or perform such modification with merely ordinary, if any, experimentation.

Formulations of the pharmaceutical compositions described herein may be prepared by any method known or hereafter developed in the art of pharmacology. In general, such preparatory methods include the step of bringing the active ingredient into association with a diluent or another excipient and/or one or more other accessory ingredients, and then, if necessary and/or desirable, shaping and/or packaging the product into a desired single- or multi-dose unit.

A pharmaceutical composition in accordance with the present disclosure may be prepared, packaged, and/or sold in bulk, as a single unit dose, and/or as a plurality of single unit doses. As used herein, a "unit dose" is discrete amount of a pharmaceutical composition described herein. For example, a unit dose of a pharmaceutical composition comprises a predetermined amount of a fusion polypeptide (e.g., ones described herein) or a polynucleotide encoding a fusion polypeptide (e.g., ones described herein).

Relative amounts of any components in pharmaceutical compositions described herein, e.g., a fusion polypeptide (e.g., ones described herein) or a polynucleotide encoding a fusion polypeptide (e.g., ones described herein), a pharmaceutically acceptable excipient, and/or any additional ingredients can vary, depending upon the subject to be treated, target cells, and may also further depend upon the route by which the composition is to be administered.

E. Exemplary Uses

Methods for using any embodiments of fusion polypeptides, polynucleotides, compositions (including, e.g. pharmaceutical compositions), and/or cells are also provided herein. In some embodiments, a method comprises: (a) contacting a target cell with a polynucleotide sequence that encodes a fusion polypeptide according to any of the embodiments herein or a composition comprising such a polynucleotide sequence; and/or (b) contacting a target cell with a fusion polypeptide according to any of the embodiments herein or a composition comprising such a fusion polypeptide. In some embodiments, a polynucleotide sequence can be or comprise any nucleic acid sequence that encodes one or more fusion polypeptides as described herein.

In some embodiments, methods described herein are for reducing or inhibiting expression (e.g., activity and/or level) of MYC in a target cell upon contacting with a fusion polypeptide, polynucleotide, and/or composition described herein. In some embodiments, expression (e.g., activity and/or level) of MYC upon contacting with a fusion polypeptide, polynucleotide, and/or composition described herein can be reduced by at least 30% or more, including, e.g., at least 40%, at least 50%, at least 60%, at least 70%, at least 80%, at least 90%, at least 95%, or more (up to 100%), as compared to expression of MYC upon contacting in the absence of a fusion polypeptide, polynucleotide, and/or composition described herein (e.g., without a repression domain), or prior to contacting with such a fusion polypeptide, polynucleotide, and/or composition described herein.

In some embodiments, methods described herein are for reducing viability and/or slowing down growth of a cancer cell upon contacting with a fusion polypeptide, polynucleotide, and/or composition described herein. In some embodiments, viability and/or growth of a cancer cell upon contacting with a fusion polypeptide, polynucleotide, and/or composition described herein can be reduced by at least 30% or more, including, e.g., at least 40%, at least 50%, at least 60%, at least 70%, at least 80%, at least 90%, at least 95%, or more, as compared to viability and/or growth of a cancer cell upon contacting in the absence of a fusion polypeptide, polynucleotide, and/or composition described herein (e.g., without a repression domain), or prior to contacting with such a fusion polypeptide, polynucleotide, and/or composition described herein.

In some embodiments, methods described herein are for increasing cancer cell killing upon contacting with a fusion polypeptide, polynucleotide, and/or composition described herein. In some embodiments, cancer cell killing upon contacting with a fusion polypeptide, polynucleotide, and/or composition described herein can be increased by at least 30% or more, including, e.g., at least 40%, at least 50%, at least 60%, at least 70%, at least 80%, at least 90%, at least 95%, or more, as compared to cancer cell killing upon contacting in the absence of a fusion polypeptide, polynucleotide, and/or composition described herein (e.g., without a repression domain), or prior to contacting with such a fusion polypeptide, polynucleotide, and/or composition described herein.

Methods described herein can be used for in vitro, ex vivo and in vivo applications. Thus, cells to which fusion peptides, polynucleotides, and/or compositions described herein are delivered can be, for example, cells cultured in vitro or ex vivo, cells within a tissue, or cells present in a subject or organism. In some embodiments, cells to which fusion peptides, polynucleotides, and/or compositions described herein are delivered can be cancer cells.

Fusion peptides, polynucleotides, and/or compositions described herein used in any methods described herein can be delivered to cells by known methods in the art, including, but not limited to, transfection into cells (e.g., via electroporation, chemical methods, etc.), delivery via particles (e.g., nanoparticles or liposomes), and/or administration to an organism (e.g., by any suitable administration route).

In some embodiments, cells subjected to a method described herein are present in a subject. Therefore, in these embodiments, a target cell present in a subject is contacted with a fusion peptide, polynucleotide, and/or composition described herein by administering such a fusion peptide, polynucleotide, and/or composition described herein to the subject.

In some embodiments, a cancer cell receiving a fusion peptide, polynucleotide, and/or composition described herein is a cancer cell expressing Myc. In some embodiments, expression and/or activity of a Myc polypeptide in a Myc-expressing cancer cell is at least 30% or more (including, e.g., at least 40%, at least 50%, at least 60%, at least 70%, at least 80%, at least 90%, at least 95%, or more) than that in a non-cancerous cell. In some embodiments, expression and/or activity of a Myc polypeptide in a Myc-expressing cancer cell is at least 1.1-fold or more (including, e.g., at least 1.5-fold, at least 2-fold, at least 3-fold, at least 4-fold, at least 5-fold, or more) than that in a non-cancerous cell.

In some embodiments, a cancer cell to be treated by a method described herein is from leukemia, neuroblastoma, lymphoma, breast cancer, colon cancer, lung cancer, ovarian cancer, thymoma, germ cell tumor, myeloma, melanoma, rectal cancer, stomach cancer, pancreatic cancer, testicular cancer, skin cancer, sarcoma, or brain cancer.

In some embodiments, fusion peptides, polynucleotides, and/or compositions described herein can be administered in combination with an additional cancer therapy, e.g., chemotherapy, radiation therapy, and/or surgery.

EXEMPLIFICATION

Example 1—Exemplary Fusion Polypeptide Comprising a Mutant MYC and a Repressor Domain (e.g., a Transcriptional Repressor) or Polynucleotide Comprising the Same The present Example demonstrates that a fusion polypeptide comprising a mutant MYC and a repressor domain increases cancer cell killing, as compared to that observed in the absence of such a fusion polypeptide or in the presence of a mutant MYC polypeptide without a repressor domain. The present Example further demonstrates that delivery of a plasmid encoding a mutant MYC polypeptide fused to a repressor domain increases cancer cell killing, as compared to a mutant MYC polypeptide alone. Although this study used a Krüppel-associated box (KRAB) repressor domain, the results can be further extended to Myc-modulating fusion polypeptides with other repressor domains.

In particular, the present Example utilized an exemplary mutant MYC polypeptide Omomyc and an exemplary fusion polypeptide comprising Omomyc and KRAB. Cancer cells were co-transfected with (i) a plasmid encoding a GFP reporter gene, and (ii) a plasmid encoding either Omomyc, Omomyc-KRAB, or an empty control plasmid. Overall GFP expression was determined 72 to 120 hours after transfection through quantification of fluorescent signal.

Preparation of Polynucleotide Sequences Encoding Polypeptides Comprising a Mutant MYC Domain Alone or a Mutant MYC Domain Fused to a Repressor Polypeptide Cloning: GFP was amplified from phMGFP (Promega) with GFP_forward and GFP_reverse primers using 2-step PCR with Phusion High-Fidelity DNA Polymerase (New England BioLabs) and cloned into pcDNA3.1D/V5-His-TOPO using the pcDNA3.1 Directional TOPO Expression Kit. Omomyc was synthesized as a gBlock (Integrated DNA Technologies) and amplified with Omomyc_forward and Omomyc_reverse primers using 2-step PCR with Phusion High-Fidelity DNA Polymerase. Omomyc-KRAB fusion was synthesized as a gBlock and amplified with Omomyc_KRAB_forward and Omomyc_KRAB_reverse primers using Phusion High-Fidelity DNA Polymerase with an annealing temperature of 60° C. Omomyc and Omomyc-KRAB were cloned into pcDNA3.2/V5-GW/D-TOPO using the pcDNA3.2 Gateway Directional TOPO Expression Kit. A reaction was also carried out using just the pcDNA3.2/V5-GW/D-TOPO plasmid to generate an empty control vector. Plasmids were transformed into One Shot TOP10 Chemically Competent E. coli cells (ThermoFisher Scientific). Transformed bacterial cells were plated on LB Agar plates with 100 μg/mL Ampicillin (Teknova). The next day colonies were screened using the T7 primer. One colony containing each insert was grown up in LB media supplemented with 100 μg/mL Ampicillin at 37° C. overnight. Plasmids were obtained using the ZymoPURE Plasmid Miniprep Kit (Zymo Research).

An exemplary sequence of the Omomyc gBlock was as follows:

```
                                      (SEQ ID NO: 30)
TAACTTGTTCTTTTTGCAGAAGCTCAGAATAAACGCTCAACTTTGGCCAC

CATGACCGAGGAGAATGTCAAGAGGCGAACACACAACGTCTTGGAGCGCC

AGAGGAGGAACGAGCTAAAACGGAGCTTTTTTGCCCTGCGTGACCAGATC

CCGGAGTTGGAAAACAATGAAAAGGCCCCCAAGGTAGTTATCCTTAAAAA

AGCCACAGCATACATCCTGTCCGTCCAAGCAGAGACGCAAAAGCTCATTT

CTGAAATCGACTTGTTGCGGAAACAAAACGAACAGTTGAAACACAAACTT

GAACAGCTACGGAACTCTTGTGCGTAATGATAGACCAGCCTCAAGAACAC

CCGAATGGAGTCTCTAAGCTACATAATACCAACTTACACTTTACAAAATG

TTGTCCCCCAAAATGTAGCCATTCGTATCTGCTCCTAATAAAAAGAAAGT

TTCTTCACATTCT
```

An exemplary sequence of the Omomyc-KRAB (with a linker between Omomyc and KRAB) gBlock was as follows:

```
                                      (SEQ ID NO: 31)
TAACTTGTTCTTTTTGCAGAAGCTCAGAATAAACGCTCAACTTTGGCCAC

CATGACCGAGGAGAATGTCAAGAGGCGAACACACAACGTCTTGGAGCGCC

AGAGGAGGAACGAGCTAAAACGGAGCTTTTTTGCCCTGCGTGACCAGATC

CCGGAGTTGGAAAACAATGAAAAGGCCCCCAAGGTAGTTATCCTTAAAAA

AGCCACAGCATACATCCTGTCCGTCCAAGCAGAGACGCAAAAGCTCATTT

CTGAAATCGACTTGTTGCGGAAACAAAACGAACAGTTGAAACACAAACTT

GAACAGCTACGGAACTCTTGTGCGAGCGGTGGAGGAAGCGGCGGATCTGG

ATCCATGGATGCTAAGTCACTAACTGCCTGGTCCCGGACACTGGTGACCT

TCAAGGATGTATTTGTGGACTTCACCAGGGAGGAGTGGAAGCTGCTGGAC

ACTGCTCAGCAGATCGTGTACAGAAATGTGATGCTGGAGAACTATAAGAA

CCTGGTTTCCTTGGGTTATCAGCTTACTAAGCCAGATGTGATCCTCCGGT

TGGAGAAGGGAGAAGAGCCCTGGCTGGTGGAGAGAGAAATTCACCAAGAG

ACCCATCCTGATTCAGAGACTGCATTTGAAATCAAATCATCAGTTTAATG

ATAGACCAGCCTCAAGAACACCCGAATGGAGTCTCTAAGCTACATAATAC

CAACTTACACTTTACAAAATGTTGTCCCCCAAAATGTAGCCATTCGTATC

TGCTCCTAATAAAAAGAAAGTTTCTTCACATTCT
```

Exemplary sequences of primers (5' to 3') used were as follows:

```
GFP_forward:
                                      (SEQ ID NO: 32)
CACCATGGGCGTGATCAAGCCCGACATG GFP_reverse:
                                      (SEQ ID NO: 33)
TTAGCCGGCCTGGCGGGGTAGT Omomyc_forward:
                                      (SEQ ID NO: 34)
CACCATGACCGAGGAGAATGTCAAGAGG Omomyc_reverse:
                                      (SEQ ID NO: 35)
TTACGCACAAGAGTTCCGTAGCTGTTCAAG Omomyc_KRAB_forward:
                                      (SEQ ID NO: 36)
CACCATGACCGAGGAGAATG Omomyc_KRAB_reverse:
                                      (SEQ ID NO: 37)
TTAAACTGATGATTTGATTTCAAATGCAGTC T7:
                                      (SEQ ID NO: 38)
TAATACGACTCACTATAGGG
```

Exemplary Transfection of Target Cells with Plasmids Encoding Polypeptides Comprising a Mutant MYC Domain Alone or a Mutant MYC Domain Fused to a Repressor Polypeptide Cancer cells, e.g., A549 cells (ATCC), were cultured in high glucose GlutaMAX Dulbecco's Modified Eagle Medium (ThermoFisher Scientific) supplemented with 10% heat-inactivated fetal bovine serum, 100 units/mL penicillin, and 100 units/mL streptomycin and maintained at 37 C and 5% CO2. Cells were plated in 96-well black clear-bottom plates (Costar) at 5,000 cells/well one day prior to transfection. Co-transfections were carried out with 25 ng GFP plasmid and 25 ng empty control, Omomyc, or Omomyc-KRAB plasmid per well using Lipofectamine™ 3000 (ThermoFisher Scientific) at a ratio of 3 μL Lipofectamine™ 3000 reagent to 2 μL P3000 Reagent to 1 μg DNA. 72 and 120 hours following transfection, cells were imaged using the GFP channel of the Cytation 5 Cell Imaging Multi-Mode Reader (BioTek). Data analysis was performed using Gen5 Microplate Reader and Imaging Software to measure the total GFP signal from GFP-positive cells.

Results

Figure 1B:
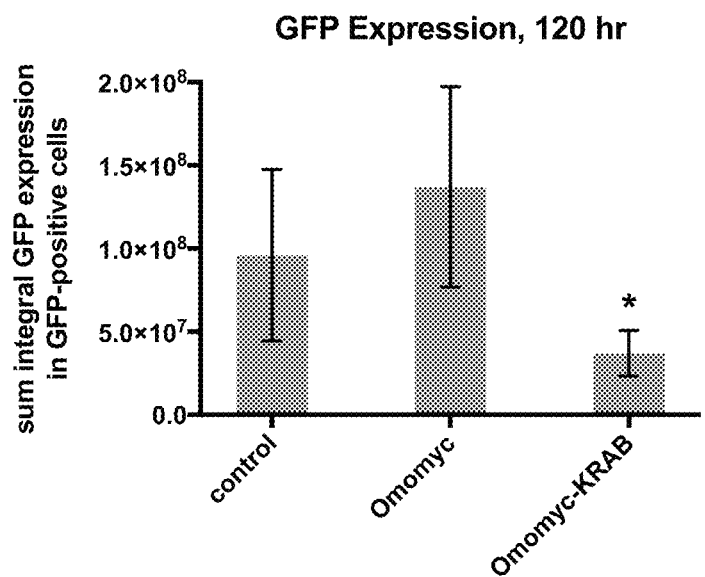

As shown in FIGS. 1A-1B, a significant ($p<0.05$, $n=3$ replicate transfections) decrease in the total GFP signal was observed when cells were co-transfected with plasmids encoding a Omomyc-KRAB fusion compared to Omomyc alone, indicating that Omomyc-KRAB fusions were more effective in killing cancer cells, relative to Omomyc alone.

Example 2—Exemplary Fusion Polypeptide Comprising a Mutant MYC and a Nuclear Localization Signal Domain or Polynucleotide Comprising the Same The present Example demonstrates that a fusion polypeptide comprising a mutant MYC and a nuclear localization signal (NLS) domain increases cancer cell killing, as compared to that observed in the absence of such a fusion polypeptide or in the presence of a mutant MYC polypeptide without a NLS domain. The present Example further demonstrates that delivery of a plasmid encoding a mutant MYC polypeptide fused to a NLS domain increases cancer cell killing, as compared to a mutant MYC polypeptide alone.

In particular, the present Example utilized an exemplary mutant MYC polypeptide Omomyc and an exemplary fusion polypeptide comprising Omomyc with an NLS fused to its N or C terminus. Cancer cells were co-transfected with (i) a plasmid encoding a GFP reporter gene, and (ii) a plasmid encoding either Omomyc, Omomyc-NLS, NLS-Omomyc, or an empty control plasmid. Overall GFP expression was determined 72 to 120 hours after transfection through quantification of fluorescent signal.

Preparation of Polynucleotide Sequences Encoding the Polypeptides Comprising a Mutant MYC Domain or a Mutant MYC Domain Fused to a NLS Domain Cloning: GFP was amplified from phMGFP (Promega) with GFP_forward and GFP_reverse primers using 2-step PCR with Phusion High-Fidelity DNA Polymerase (New England BioLabs). Omomyc was synthesized as a gBlock (Integrated DNA Technologies) and amplified with Omomyc_forward and Omomyc_reverse primers using 2-step PCR with Phusion High-Fidelity DNA Polymerase. NLS-Omomyc and Omomyc-NLS fusions were synthesized as gBlocks. GFP, Omomyc, NLS-Omomyc, and Omomyc-NLS were cloned into pcDNA3.1D/V5-His-TOPO using the pcDNA3.1 Directional TOPO Expression Kit and transformed into One Shot TOP10 Chemically Competent E. coli cells (ThermoFisher Scientific). A reaction was also carried out using just the pcDNA3.1D/V5-His-TOPO plasmid to generate an empty control vector. Transformed bacterial cells were plated on LB Agar plates with 100 ug/mL Ampicillin (Teknova). The next day colonies were screened using the T7 primer. One colony containing each insert was grown up in LB media supplemented with 100 ug/mL Ampicillin at 37° C. overnight. Plasmids were obtained using the ZymoPURE Plasmid Miniprep Kit (Zymo Research).

An exemplary sequence of the Omomyc gBlock was as follows:

(SEQ ID NO: 30)
TAACTTGTTCTTTTTGCAGAAGCTCAGAATAAACGCTCAACTTTGGCCAC

CATGACCGAGGAGAATGTCAAGAGGCGAACACACAACGTCTTGGAGCGCC

AGAGGAGGAACGAGCTAAAACGGAGCTTTTTTGCCCTGCGTGACCAGATC

CCGGAGTTGGAAAACAATGAAAAGGCCCCCAAGGTAGTTATCCTTAAAAA

AGCCACAGCATACATCCTGTCCGTCCAAGCAGAGACGCAAAAGCTCATTT

CTGAAATCGACTTGTTGCGGAAACAAAACGAACAGTTGAAACACAAACTT

GAACAGCTACGGAACTCTTGTGCGTAATGATAGACCAGCCTCAAGAACAC

CCGAATGGAGTCTCTAAGCTACATAATACCAACTTACACTTTACAAAATG

TTGTCCCCCAAAATGTAGCCATTCGTATCTGCTCCTAATAAAAAGAAAGT

TTCTTCACATTCT

An exemplary sequence of the NLS-Omomyc (including a linker) gBlock was as follows:

(SEQ ID NO: 39)
CACCATGCCTGCAGCAAAACGGGTGAAACTTGATGGCGGGGGGGGTTCTG

GTGGAGGAGGAAGCGGTGGAGGTGGGTCTACCGAGGAGAATGTCAAGAGG

CGAACACACAACGTCTTGGAGCGCCAGAGGAGGAACGAGCTGAAACGGAG

CTTTTTTGCCCTGAGAGACCAGATCCCGGAGTTGGAAAACAATGAAAGG

CCCCCAAGGTAGTTATCCTTAAAAAAGCCACAGCATACATCCTGTCCGTC

CAAGCAGAGACGCAAAAGCTCATTTCTGAAATCGACTTGTTGCGGAAACA

AAACGAACAGTTGAAACACAAACTTGAACAGCTGCGGAACTCTTGTGCGT

AATGATAG

An exemplary sequence of the Omomyc-NLS (including a linker) gBlock was as follows:

(SEQ ID NO: 40)
CACCATGACCGAGGAGAATGTCAAGAGGCGAACACACAACGTCTTGGAGC

GCCAGAGGAGGAACGAGCTGAAACGGAGCTTTTTTGCCCTGAGAGACCAG

ATCCCGGAGTTGGAAAACAATGAAAAGGCCCCCAAGGTAGTTATCCTTAA

AAAAGCCACAGCATACATCCTGTCCGTCCAAGCAGAGACGCAAAAGCTCA

TTTCTGAAATCGACTTGTTGCGGAAACAAAACGAACAGTTGAAACACAAA

CTTGAACAGCTGCGGAACTCTTGTGCGGGCGGGGGGGTTCTGGTGGAGG

AGGAAGCGGTGGAGGTGGGTCTCCTGCAGCAAAACGGGTGAAACTTGATT

AATGATAG

Exemplary sequences of primers used were as follows:

```
GFP_forward:
                                   (SEQ ID NO: 32)
CACCATGGGCGTGATCAAGCCCGACATG GFP_reverse:
                                   (SEQ ID NO: 33)
TTAGCCGGCCTGGCGGGGTAGT Omomyc_forward:
                                   (SEQ ID NO: 34)
CACCATGACCGAGGAGAATGTCAAGAGG Omomyc_reverse:
                                   (SEQ ID NO: 35)
TTACGCACAAGAGTTCCGTAGCTGTTCAAG

T7:
                                   (SEQ ID NO: 38)
TAATACGACTCACTATAGGG
```

Exemplary Transfection of Target Cells with Plasmids Encoding Polypeptides Comprising a Mutant MYC Domain Alone or a Mutant Myc Domain Fused to a NLS Domain.

Cancer cells (e.g., A549 cells (ATCC)) were cultured in high glucose GlutaMAX Dulbecco's Modified Eagle Medium (ThermoFisher Scientific) supplemented with 10% heat-inactivated fetal bovine serum, 100 units/mL penicillin, and 100 units/mL streptomycin and maintained at 37° C. and 5% CO2. Cells were plated in 96-well black clear-bottom plates (Costar) at 5,000 cells/well one day prior to transfection. Co-transfections were carried out with 25 ng GFP plasmid and 25 ng empty control, Omomyc, NLS-Omomyc, or Omomyc-NLS plasmid per well using Lipofectamine™ 3000 (ThermoFisher Scientific) at a ratio of 3 μL Lipofectamine™ 3000 reagent to 2 μL P3000 Reagent to 1 μg DNA. 72 hours following transfection, cells were imaged using the GFP channel of the Cytation 5 Cell Imaging Multi-Mode Reader (BioTek). Data analysis was performed using Gen5 Microplate Reader and Imaging Software to count the number of GFP-positive cells.

Results

Figure 2:
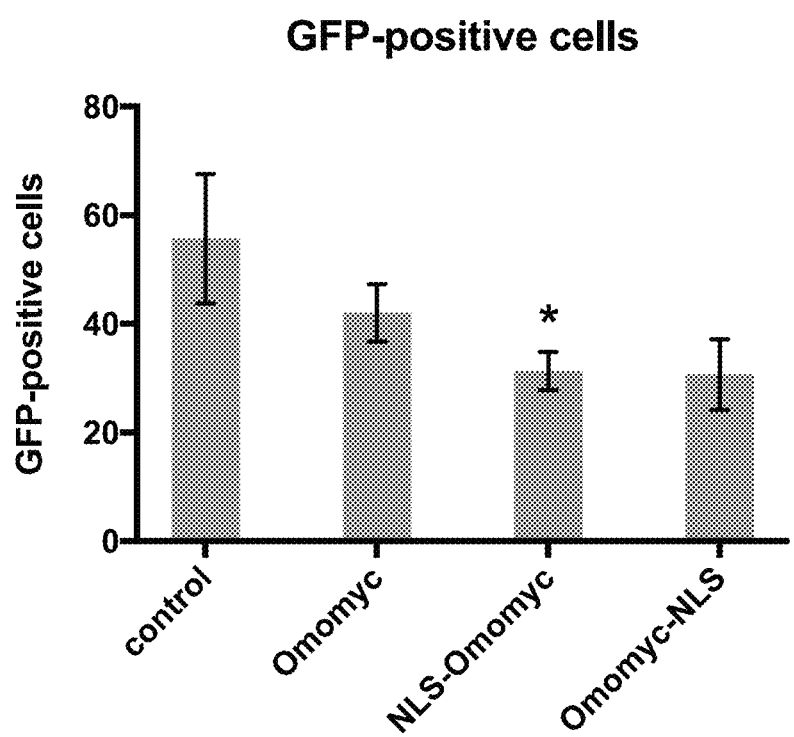
FIG. 2 depicts expression of a GFP target when a plasmid encoding either no polypeptide (control), a polypeptide containing mutant MYC (Omomyc), or a fusion polypeptide containing mutant MYC fused to a nuclear localization signal domain at the N or C terminus is transfected into cells. A reduced number of GFP-positive cells (y-axis) relative to the control indicates repression of GFP expression by the polypeptide.

As shown in FIG. 2, a statistically significant decrease ($p<0.05$, $n=3$ replicate transfections) in the number of GFP-expressing cells was observed when co-transfected with plasmids encoding NLS-Omomyc compare to Omomyc alone. Similarly, a decrease ($p<0.08$, $n=3$ replicate transfections) in the number of GFP-expressing cells was observed when co-transfected with plasmids encoding Omomyc-NLS fusion compared to Omomyc alone. These results indicate that fusing an Omomyc to a native c-MYC nuclear localization signal domain increases toxicity of Omomyc and thus NLS-Omomyc or Omomyc-NLS fusions are more effective in killing cancer cells, as compared to Omomyc alone.

Example 3—Other Exemplary Fusion Polypeptides Comprising a Mutant MYC Domain and One or More Functional Domains of Interest Optionally With One or More Linker Sequences In some embodiments, the present Example includes assessing the characteristics of adding a C-terminal c-MYC nuclear localization signal domain to a fusion polypeptide comprising a mutant MYC (e.g., Omomyc) and a repressor domain (e.g., KRAB).

In some embodiments, the present Example describes an experimental screen of fusion polypeptides comprising a mutant MYC domain and one or more functional domains (e.g., repressor domains) optionally using one or more linkers, or any combination thereof. Exemplary repressor domains are screened through in vitro measurements of a reporter protein expression similar to the method described in Examples 1 and 2. Exemplary repressor domains that are screened include, but are not limited to the following:

- mSIN interaction domain (SID) (Ayer et al., Mol Cell Biol 1996, which is incorporated by reference in its entirety) and SID4X (Konermann et al., Nature 2014, which is incorporated by reference in its entirety);
- RE1-Silencing Transcription Factor (REST) repressor domain (Thiel et al., J Biol Chem 1998, which is incorporated by reference in its entirety);
- thyroid hormone receptor repression domains (Thiel et al., Biol Chem 2001, which is incorporated by reference in its entirety);
- Egr-1 repression domains (Gashler et al., Mol Cell Biol 1993, which is incorporated by reference in its entirety);
- $YY_1$ (Shi et al., Cell 1991, which is incorporated by reference in its entirety);
- hairy protein family repression motif (Fisher et al., Mol Cell Biol 1996, which is incorporated by reference in its entirety);
- Engrailed homology-1 repression motif (Smith et al., Development 1996, which is incorporated by reference in its entirety);
- human TLE proteins (Jennings et al., Genome Biol 2008, which is incorporated by reference in its entirety);
- histone deacetylase 2 (HDAC2) (Thiel et al., Biol Chem 2001, which is incorporated by reference in its entirety);
- Sir2 (Loo et al., Annu Rev Cell Dev Biol 1995, which is incorporated by reference in its entirety), and combinations thereof.

In some embodiments, the present Example includes characterization of fusion polypeptides comprising a mutant MYC and different copy numbers (e.g., at least 1, at least 2, at least 3, at least 4, or more) and combinations of repressor domains (e.g., ones as described herein).

In some embodiments, the present Example includes screening different functional domains of interest, including, but not limited to, nuclear localization signal domains or combinations of the same, and/or cell-penetrating peptides and/or secretion tags such as human serum albumin signal peptide.

In some embodiments, the present Example discloses screening of different linker architectures between domains (e.g., a linker between a mutant MYC and a repressor domain), including, but not limited to, flexible glycine-serine linkers, native c-MYC linker sequences, and/or various linker length combinations thereof.

In some embodiments, the present Example discloses screening of fusion polypeptide architecture, including, but not limited to order of domains (e.g., a mutant MYC is 5' or 3' of a repressor domain) and/or copy number of each domains.

In some embodiments, the present Example includes screening and assessing of fusion polypeptides comprising non-mutant or mutant, truncated MYC polypeptides (e.g., one or more of MYC basic region, helix-loop-helix, leucine-zipper domains) fused to one or more functional domains of interest (e.g., a repressor domain such as, e.g., ones described herein). In some embodiments, a mutant MYC polypeptide may have improved homodimerization or DNA-binding capabilities.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

Those skilled in the art will recognize, or be able to ascertain using no more than routine experimentation, many equivalents to the specific embodiments of the invention described herein. It is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Further, it should also be understood that any embodiment or aspect of the invention can be explicitly excluded from the claims, regardless of whether the specific exclusion is recited in the specification. The scope of the present invention is not intended to be limited to the above Description, but rather is as set forth in the claims that follow.

What is claimed is:

1. A fusion polypeptide comprising a mutant dominant negative MYC polypeptide and a repressor domain, wherein the fusion polypeptide comprises the amino acid sequence of SEQ ID NO: 29.

2. An ex vivo cell comprising the fusion polypeptide of claim 1.

3. The fusion polypeptide of claim 1, further comprising a functional domain.

4. The fusion polypeptide of claim 3, wherein the functional domain is: a repressor domain, a nuclear localization signal domain, a cell penetrating peptide, a detectable or secretion label, a protein-protein interaction domain, or any combination thereof.

5. The fusion polypeptide of claim 3, wherein the functional domain comprises a nuclear localization signal domain of MYC.

6. The fusion polypeptide of claim 3, wherein the functional domain comprises a second repressor domain.

7. A polynucleotide comprising a nucleic acid sequence encoding a fusion polypeptide comprising a mutant dominant negative MYC polypeptide and a repressor domain, wherein the fusion polypeptide comprises the amino acid sequence of SEQ ID NO: 29.

8. The polynucleotide of claim 7, wherein the nucleic acid sequence is RNA.

9. The polynucleotide of claim 7, wherein the nucleic acid sequence is DNA.

10. A composition comprising the polynucleotide of claim 7, wherein the composition comprises a delivery vehicle.

11. The composition of claim 10, wherein the polynucleotide is included in an expression vector.

12. An ex vivo cell comprising the polynucleotide of claim 7.

13. The cell of claim 12, wherein the cell is a cancer cell.

14. A pharmaceutical composition comprising the polynucleotide of claim 7 and a pharmaceutically acceptable excipient.

15. The polynucleotide of claim 7, further comprising a nucleotide sequence encoding a functional domain.

16. The polynucleotide of claim 15, wherein the encoded functional domain is a repressor domain, a nuclear localization signal domain, a cell penetrating peptide, a detectable or secretion label, a protein-protein interaction domain, or any combination thereof.

17. The polynucleotide of claim 15, wherein the encoded functional domain comprises a nuclear localization signal domain of MYC.

18. The polynucleotide of claim 15, wherein the encoded functional domain comprises a second repressor domain.

19. A method comprising contacting cells with the polynucleotide of claim 7.

20. A method comprising administering to a subject the polynucleotide of claim 7.

21. A method of making comprising:
    recombinantly joining a mutant dominant negative MYC-encoding nucleic acid and a repressor-encoding nucleic acid to form the polynucleotide of claim 7.

* * * * *

SEQUENCE LISTING

```
<160> NUMBER OF SEQ ID NOS: 40

<210> SEQ ID NO 1
<211> LENGTH: 439
<212> TYPE: PRT
<213> ORGANISM: Homo sapiens

<400> SEQUENCE: 1

Met Pro Leu Asn Val Ser Phe Thr Asn Arg Asn Tyr Asp Leu Asp Tyr
1               5                   10                  15

Asp Ser Val Gln Pro Tyr Phe Tyr Cys Asp Glu Glu Glu Asn Phe Tyr
                20                  25                  30

Gln Gln Gln Gln Gln Ser Glu Leu Gln Pro Pro Ala Pro Ser Glu Asp
            35                  40                  45

Ile Trp Lys Lys Phe Glu Leu Leu Pro Thr Pro Pro Leu Ser Pro Ser
    50                  55                  60

Arg Arg Ser Gly Leu Cys Ser Pro Ser Tyr Val Ala Val Thr Pro Phe
65                  70                  75                  80

Ser Leu Arg Gly Asp Asn Asp Gly Gly Gly Ser Phe Ser Thr Ala
                85                  90                  95

Asp Gln Leu Glu Met Val Thr Glu Leu Leu Gly Gly Asp Met Val Asn
                100                 105                 110

Gln Ser Phe Ile Cys Asp Pro Asp Asp Glu Thr Phe Ile Lys Asn Ile
            115                 120                 125

Ile Ile Gln Asp Cys Met Trp Ser Gly Phe Ser Ala Ala Ala Lys Leu
    130                 135                 140

Val Ser Glu Lys Leu Ala Ser Tyr Gln Ala Ala Arg Lys Asp Ser Gly
145                 150                 155                 160

Ser Pro Asn Pro Ala Arg Gly His Ser Val Cys Ser Thr Ser Ser Leu
```

-continued

```
                165                 170                 175
Tyr Leu Gln Asp Leu Ser Ala Ala Ser Glu Cys Ile Asp Pro Ser
            180                 185                 190

Val Val Phe Pro Tyr Pro Leu Asn Asp Ser Ser Pro Lys Ser Cys
            195                 200                 205

Ala Ser Gln Asp Ser Ser Ala Phe Ser Pro Ser Ser Asp Ser Leu Leu
            210                 215                 220

Ser Ser Thr Glu Ser Ser Pro Gln Gly Ser Pro Glu Pro Leu Val Leu
225                 230                 235                 240

His Glu Glu Thr Pro Pro Thr Thr Ser Ser Asp Ser Glu Glu Glu Gln
                245                 250                 255

Glu Asp Glu Glu Glu Ile Asp Val Val Ser Val Glu Lys Arg Gln Ala
                260                 265                 270

Pro Gly Lys Arg Ser Glu Ser Gly Ser Pro Ser Ala Gly Gly His Ser
                275                 280                 285

Lys Pro Pro His Ser Pro Leu Val Leu Lys Arg Cys His Val Ser Thr
            290                 295                 300

His Gln His Asn Tyr Ala Ala Pro Pro Ser Thr Arg Lys Asp Tyr Pro
305                 310                 315                 320

Ala Ala Lys Arg Val Lys Leu Asp Ser Val Arg Val Leu Arg Gln Ile
                325                 330                 335

Ser Asn Asn Arg Lys Cys Thr Ser Pro Arg Ser Ser Asp Thr Glu Glu
                340                 345                 350

Asn Val Lys Arg Arg Thr His Asn Val Leu Glu Arg Gln Arg Arg Asn
                355                 360                 365

Glu Leu Lys Arg Ser Phe Phe Ala Leu Arg Asp Gln Ile Pro Glu Leu
            370                 375                 380

Glu Asn Asn Glu Lys Ala Pro Lys Val Val Ile Leu Lys Lys Ala Thr
385                 390                 395                 400

Ala Tyr Ile Leu Ser Val Gln Ala Glu Glu Gln Lys Leu Ile Ser Glu
                405                 410                 415

Glu Asp Leu Leu Arg Lys Arg Arg Glu Gln Leu Lys His Lys Leu Glu
                420                 425                 430

Gln Leu Arg Asn Ser Cys Ala
            435

<210> SEQ ID NO 2
<211> LENGTH: 464
<212> TYPE: PRT
<213> ORGANISM: Homo sapiens

<400> SEQUENCE: 2

Met Pro Ser Cys Ser Thr Ser Thr Met Pro Gly Met Ile Cys Lys Asn
1               5                   10                  15

Pro Asp Leu Glu Phe Asp Ser Leu Gln Pro Cys Phe Tyr Pro Asp Glu
                20                  25                  30

Asp Asp Phe Tyr Phe Gly Gly Pro Asp Ser Thr Pro Pro Gly Glu Asp
            35                  40                  45

Ile Trp Lys Lys Phe Glu Leu Leu Pro Thr Pro Pro Leu Ser Pro Ser
        50                  55                  60

Arg Gly Phe Ala Glu His Ser Ser Glu Pro Pro Ser Trp Val Thr Glu
65                  70                  75                  80

Met Leu Leu Glu Asn Glu Leu Trp Gly Ser Pro Ala Glu Glu Asp Ala
                85                  90                  95
```

```
Phe Gly Leu Gly Gly Leu Gly Gly Leu Thr Pro Asn Pro Val Ile Leu
                100                 105                 110

Gln Asp Cys Met Trp Ser Gly Phe Ser Ala Arg Glu Lys Leu Glu Arg
            115                 120                 125

Ala Val Ser Glu Lys Leu Gln His Gly Arg Gly Pro Pro Thr Ala Gly
        130                 135                 140

Ser Thr Ala Gln Ser Pro Gly Ala Gly Ala Ser Pro Ala Gly Arg
145                 150                 155                 160

Gly His Gly Gly Ala Gly Ala Gly Arg Ala Gly Ala Ala Leu Pro
                165                 170                 175

Ala Glu Leu Ala His Pro Ala Ala Glu Cys Val Asp Pro Ala Val Val
            180                 185                 190

Phe Pro Phe Pro Val Asn Lys Arg Glu Pro Ala Pro Val Pro Ala Ala
        195                 200                 205

Pro Ala Ser Ala Pro Ala Ala Gly Pro Ala Val Ala Ser Gly Ala Gly
210                 215                 220

Ile Ala Ala Pro Ala Gly Ala Pro Gly Val Ala Pro Arg Pro Gly
225                 230                 235                 240

Gly Arg Gln Thr Ser Gly Gly Asp His Lys Ala Leu Ser Thr Ser Gly
                245                 250                 255

Glu Asp Thr Leu Ser Asp Ser Asp Asp Glu Asp Glu Glu Glu Asp
            260                 265                 270

Glu Glu Glu Glu Ile Asp Val Val Thr Val Glu Lys Arg Arg Ser Ser
        275                 280                 285

Ser Asn Thr Lys Ala Val Thr Thr Phe Thr Ile Thr Val Arg Pro Lys
290                 295                 300

Asn Ala Ala Leu Gly Pro Gly Arg Ala Gln Ser Ser Glu Leu Ile Leu
305                 310                 315                 320

Lys Arg Cys Leu Pro Ile His Gln Gln His Asn Tyr Ala Ala Pro Ser
                325                 330                 335

Pro Tyr Val Glu Ser Glu Asp Ala Pro Pro Gln Lys Lys Ile Lys Ser
            340                 345                 350

Glu Ala Ser Pro Arg Pro Leu Lys Ser Val Ile Pro Pro Lys Ala Lys
        355                 360                 365

Ser Leu Ser Pro Arg Asn Ser Asp Ser Glu Asp Ser Glu Arg Arg Arg
370                 375                 380

Asn His Asn Ile Leu Glu Arg Gln Arg Arg Asn Asp Leu Arg Ser Ser
385                 390                 395                 400

Phe Leu Thr Leu Arg Asp His Val Pro Glu Leu Val Lys Asn Glu Lys
                405                 410                 415

Ala Ala Lys Val Val Ile Leu Lys Lys Ala Thr Glu Tyr Val His Ser
            420                 425                 430

Leu Gln Ala Glu Glu His Gln Leu Leu Leu Glu Lys Glu Lys Leu Gln
        435                 440                 445

Ala Arg Gln Gln Gln Leu Leu Lys Lys Ile Glu His Ala Arg Thr Cys
450                 455                 460

<210> SEQ ID NO 3
<211> LENGTH: 364
<212> TYPE: PRT
<213> ORGANISM: Homo sapiens

<400> SEQUENCE: 3

Met Asp Tyr Asp Ser Tyr Gln His Tyr Phe Tyr Asp Tyr Asp Cys Gly
1               5                   10                  15
```

```
Glu Asp Phe Tyr Arg Ser Thr Ala Pro Ser Glu Asp Ile Trp Lys Lys
             20                  25                  30

Phe Glu Leu Val Pro Ser Pro Thr Ser Pro Trp Gly Leu Gly
         35                  40                  45

Pro Gly Ala Gly Asp Pro Ala Pro Gly Ile Gly Pro Pro Glu Pro Trp
 50                  55                  60

Pro Gly Gly Cys Thr Gly Asp Glu Ala Glu Ser Arg Gly His Ser Lys
 65                  70                  75                  80

Gly Trp Gly Arg Asn Tyr Ala Ser Ile Ile Arg Arg Asp Cys Met Trp
                 85                  90                  95

Ser Gly Phe Ser Ala Arg Glu Arg Leu Glu Arg Ala Val Ser Asp Arg
            100                 105                 110

Leu Ala Pro Gly Ala Pro Arg Gly Asn Pro Lys Ala Ser Ala Ala
            115                 120                 125

Pro Asp Cys Thr Pro Ser Leu Glu Ala Gly Asn Pro Ala Pro Ala Ala
130                 135                 140

Pro Cys Pro Leu Gly Glu Pro Lys Thr Gln Ala Cys Ser Gly Ser Glu
145                 150                 155                 160

Ser Pro Ser Asp Ser Glu Asn Glu Glu Ile Asp Val Val Thr Val Glu
                165                 170                 175

Lys Arg Gln Ser Leu Gly Ile Arg Lys Pro Val Thr Ile Thr Val Arg
            180                 185                 190

Ala Asp Pro Leu Asp Pro Cys Met Lys His Phe His Ile Ser Ile His
            195                 200                 205

Gln Gln Gln His Asn Tyr Ala Ala Arg Phe Pro Pro Glu Ser Cys Ser
            210                 215                 220

Gln Glu Glu Ala Ser Glu Arg Gly Pro Gln Glu Val Leu Glu Arg
225                 230                 235                 240

Asp Ala Ala Gly Glu Lys Glu Asp Glu Glu Asp Glu Glu Ile Val Ser
                245                 250                 255

Pro Pro Pro Val Glu Ser Glu Ala Ala Gln Ser Cys His Pro Lys Pro
            260                 265                 270

Val Ser Ser Asp Thr Glu Asp Val Thr Lys Arg Lys Asn His Asn Phe
            275                 280                 285

Leu Glu Arg Lys Arg Arg Asn Asp Leu Arg Ser Arg Phe Leu Ala Leu
290                 295                 300

Arg Asp Gln Val Pro Thr Leu Ala Ser Cys Ser Lys Ala Pro Lys Val
305                 310                 315                 320

Val Ile Leu Ser Lys Ala Leu Glu Tyr Leu Gln Ala Leu Val Gly Ala
                325                 330                 335

Glu Lys Arg Met Ala Thr Glu Lys Arg Gln Leu Arg Cys Arg Gln Gln
            340                 345                 350

Gln Leu Gln Lys Arg Ile Ala Tyr Leu Thr Gly Tyr
            355                 360

<210> SEQ ID NO 4
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Thr Glu Glu Asn Val Lys Arg Arg Thr His Asn Val Leu Glu Arg Gln
```

```
                1               5                   10                  15
Arg Arg Asn Glu Leu Lys Arg Ser Phe Phe Ala Leu Arg Asp Gln Ile
                20                  25                  30

Pro Glu Leu Glu Asn Asn Glu Lys Ala Pro Lys Val Val Ile Leu Lys
            35                  40                  45

Lys Ala Thr Ala Tyr Ile Leu Ser Val Gln Ala Glu Glu Gln Lys Leu
        50                  55                  60

Ile Ser Glu Glu Asp Leu Leu Arg Lys Arg Arg Glu Gln Leu Lys His
65                  70                  75                  80

Lys Leu Glu Gln Leu Arg Asn Ser Cys Ala
                85                  90

<210> SEQ ID NO 5
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ser Glu Asp Ser Glu Arg Arg Asn His Asn Ile Leu Glu Arg Gln
1               5                   10                  15

Arg Arg Asn Asp Leu Arg Ser Ser Phe Leu Thr Leu Arg Asp His Val
                20                  25                  30

Pro Glu Leu Val Lys Asn Glu Lys Ala Ala Lys Val Val Ile Leu Lys
            35                  40                  45

Lys Ala Thr Glu Tyr Val His Ser Leu Gln Ala Glu Glu His Gln Leu
        50                  55                  60

Leu Leu Glu Lys Glu Lys Leu Gln Ala Arg Gln Gln Gln Leu Leu Lys
65                  70                  75                  80

Lys Ile Glu His Ala Arg Thr Cys
                85

<210> SEQ ID NO 6
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Thr Glu Asp Val Thr Lys Arg Lys Asn His Asn Phe Leu Glu Arg Lys
1               5                   10                  15

Arg Arg Asn Asp Leu Arg Ser Arg Phe Leu Ala Leu Arg Asp Gln Val
                20                  25                  30

Pro Thr Leu Ala Ser Cys Ser Lys Ala Pro Lys Val Val Ile Leu Ser
            35                  40                  45

Lys Ala Leu Glu Tyr Leu Gln Ala Leu Val Gly Ala Glu Lys Arg Met
        50                  55                  60

Ala Thr Glu Lys Arg Gln Leu Arg Cys Arg Gln Gln Gln Leu Gln Lys
65                  70                  75                  80

Arg Ile Ala Tyr Leu Thr Gly Tyr
                85

<210> SEQ ID NO 7
<211> LENGTH: 97
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 7

Met Asp Ala Lys Ser Leu Thr Ala Trp Ser Arg Thr Leu Val Thr Phe
1               5                   10                  15

Lys Asp Val Phe Val Asp Phe Thr Arg Glu Glu Trp Lys Leu Leu Asp
            20                  25                  30

Thr Ala Gln Gln Ile Val Tyr Arg Asn Val Met Leu Glu Asn Tyr Lys
        35                  40                  45

Asn Leu Val Ser Leu Gly Tyr Gln Leu Thr Lys Pro Asp Val Ile Leu
    50                  55                  60

Arg Leu Glu Lys Gly Glu Glu Pro Trp Leu Val Glu Arg Glu Ile His
65                  70                  75                  80

Gln Glu Thr His Pro Asp Ser Glu Thr Ala Phe Glu Ile Lys Ser Ser
                85                  90                  95

Val

<210> SEQ ID NO 8
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Met Asn Ile Gln Met Leu Leu Glu Ala Ala Asp Tyr Leu Glu Arg Arg
1               5                   10                  15

Glu Arg Glu Ala Glu His Gly Tyr Ala Ser Met Leu Pro
            20                  25

<210> SEQ ID NO 9
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Asn Ile Gln Met Leu Leu Glu Ala Ala Asp Tyr Leu Glu Arg Arg
1               5                   10                  15

Glu Arg Glu Ala Glu His Gly Tyr Ala Ser Met Leu Pro Gly Ser Gly
            20                  25                  30

Met Asn Ile Gln Met Leu Leu Glu Ala Ala Asp Tyr Leu Glu Arg Arg
        35                  40                  45

Glu Arg Glu Ala Glu His Gly Tyr Ala Ser Met Leu Pro Gly Ser Gly
    50                  55                  60

Met Asn Ile Gln Met Leu Leu Glu Ala Ala Asp Tyr Leu Glu Arg Arg
65                  70                  75                  80

Glu Arg Glu Ala Glu His Gly Tyr Ala Ser Met Leu Pro Gly Ser Gly
                85                  90                  95

Met Asn Ile Gln Met Leu Leu Glu Ala Ala Asp Tyr Leu Glu Arg Arg
            100                 105                 110

Glu Arg Glu Ala Glu His Gly Tyr Ala Ser Met Leu Pro
        115                 120                 125

<210> SEQ ID NO 10
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Ala Thr Gln Val Met Gly Gln Ser Ser Gly Gly Gly Leu Phe
1               5                   10                  15

Thr Ser Ser Gly Asn Ile Gly Met Ala Leu Pro Asn Asp Met Tyr Asp
            20                  25                  30

Leu His Asp Leu Ser Lys Ala Glu Leu Ala Ala Pro Gln Leu Ile Met
        35                  40                  45

Leu Ala Asn Val Ala Leu Thr Gly Glu Val Asn Gly Ser Cys Cys Asp
    50                  55                  60

Tyr Leu Val Gly Glu Glu Arg Gln Met Ala Glu Leu Met Pro Val Gly
65                  70                  75                  80

Asp Asn Asn Phe Ser Asp Ser Glu Gly Glu Gly Leu Glu Glu Ser
                85                  90                  95

Ala Asp Ile Lys Gly Glu Pro His Gly Leu Glu Asn Met Glu Leu Arg
            100                 105                 110

Ser Leu Glu Leu Ser Val Val Glu Pro Gln Pro Val Phe Glu Ala Ser
        115                 120                 125

Gly Ala Pro Asp Ile Tyr Ser Ser Asn Lys Asp Leu Pro Pro Glu Thr
    130                 135                 140

Pro Gly Ala Glu Asp Lys Gly Lys
145                 150

<210> SEQ ID NO 11
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Asn Thr Arg Glu Asn Leu Thr Gly Ile Asn Ser Thr Val Glu Glu
1               5                   10                  15

Pro Val Ser Pro Met Leu Pro Pro Ser Ala Val Glu Glu Arg Glu Ala
            20                  25                  30

Val Ser Lys Thr Ala Leu Ala Ser Pro Pro Ala Thr Met Ala Ala Asn
        35                  40                  45

Glu Ser Gln Glu Ile Asp Glu Asp Glu Gly Ile His Ser His Glu Gly
    50                  55                  60

Ser Asp Leu Ser Asp Asn Met Ser Glu Gly Ser Asp Ser Gly Leu
65                  70                  75                  80

His Gly Ala Arg Pro Val Pro Gln Glu Ser Arg Lys Asn Ala Lys
                85                  90                  95

Glu Ala Leu Ala Val Lys Ala Ala Lys Gly Asp Phe Val Cys Ile Phe
            100                 105                 110

Cys Asp Arg Ser Phe Arg Lys Gly Lys Asp Tyr Ser Lys His Leu Asn
        115                 120                 125

Arg His Leu Val Asn Val Tyr Tyr Leu Glu Glu Ala Ala Gln Gly Gln
    130                 135                 140

Glu
145

<210> SEQ ID NO 12
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Met Asp Leu Val Leu Asp Asp Ser Lys Arg Val Ala Lys Arg Lys Leu
1               5                   10                  15

Ile Glu Gln Asn Arg Glu Arg Arg Lys Glu Met Ile Arg Ser
                20                  25                  30

Leu Gln Gln Arg Pro Glu Pro Thr Pro Glu Glu Trp Asp Leu Ile His
            35                  40                  45

Ile Ala Thr Glu Ala His Arg Ser Thr Asn Ala Gln Gly Ser His Trp
        50                  55                  60

Lys Gln Arg Arg Lys Phe Leu Pro Asp Asp Ile Gly Gln Ser Pro Ile
65                  70                  75                  80

Val Ser Met Pro Asp Gly Asp Lys Val Asp Leu Glu Ala Phe Ser Glu
                85                  90                  95

Phe Thr Lys Ile Ile Thr Pro Ala Ile Thr Arg Val Val Asp Phe Ala
            100                 105                 110

Lys Lys Leu Pro Met Phe Ser Glu Leu Pro Cys Glu Asp Gln Ile Ile
        115                 120                 125

Leu Leu Lys Gly Cys Cys Met Glu Ile Met Ser Leu Arg Ala Ala Val
130                 135                 140

Arg Tyr Asp Pro Glu Ser Asp Thr Leu Thr Leu Ser Gly Glu Met Ala
145                 150                 155                 160

Val Lys Arg Glu Gln Leu Lys Asn Gly Gly Leu Gly Val Val Ser Asp
                165                 170                 175

Ala Ile Phe Glu Leu Gly Lys Ser Leu Ser Ala Phe Asn Leu Asp Asp
            180                 185                 190

Thr Glu Val Ala Leu Leu Gln Ala Val Leu Leu Met Ser Thr Asp Arg
        195                 200                 205

Ser Gly Leu Leu Cys Val Asp Lys Ile Glu Lys Ser Gln Glu Ala Tyr
210                 215                 220

Leu Leu Ala Phe Glu His Tyr Val Asn His Arg Lys His Asn Ile Pro
225                 230                 235                 240

His Phe Trp Pro Lys Leu Leu Met Lys Glu Arg Glu Val Gln Ser Ser
                245                 250                 255

Ile Leu Tyr Lys Gly Ala Ala Ala Glu Gly Arg Pro Gly Gly Ser Leu
            260                 265                 270

Gly Val His Pro Glu Gly Gln Gln Leu Leu Gly Met His Val Val Gln
        275                 280                 285
```

<210> SEQ ID NO 13
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Cys Arg Phe Lys Lys Cys Ile Tyr Val Gly Met Ala Thr Asp Leu Val
1               5                   10                  15

Leu Asp Asp Ser Lys Arg Leu Ala Lys Arg Lys Leu Ile Glu Glu Asn
            20                  25                  30

Arg Glu Lys Arg Arg Glu Glu Leu Gln Lys Ser Ile Gly His Lys
            35                  40                  45

Pro Glu Pro Thr Asp Glu Glu Trp Glu Leu Ile Lys Thr Val Thr Glu
        50                  55                  60

Ala His Val Ala Thr Asn Ala Gln Gly Ser His Trp Lys Gln Lys Arg
65                  70                  75                  80

Lys Phe Leu Pro Glu Asp Ile Gly Gln Ala Pro Ile Val Asn Ala Pro
                85                  90                  95

Glu Gly Gly Lys Val Asp Leu Glu Ala Phe Ser His Phe Thr Lys Ile
            100                 105                 110

Ile Thr Pro Ala Ile Thr Arg Val Val Asp Phe Ala Lys Lys Leu Pro
            115                 120                 125

Met Phe Cys Glu Leu Pro Cys Glu Asp Gln Ile Ile Leu Leu Lys Gly
        130                 135                 140

Cys Cys Met Glu Ile Met Ser Leu Arg Ala Ala Val Arg Tyr Asp Pro
145                 150                 155                 160

Glu Ser Glu Thr Leu Thr Leu Asn Gly Glu Met Ala Val Thr Arg Gly
                165                 170                 175

Gln Leu Lys Asn Gly Gly Leu Gly Val Val Ser Asp Ala Ile Phe Asp
            180                 185                 190

Leu Gly Met Ser Leu Ser Ser Phe Asn Leu Asp Asp Thr Glu Val Ala
        195                 200                 205

Leu Leu Gln Ala Val Leu Leu Met Ser Ser Asp Arg Pro Gly Leu Ala
210                 215                 220

Cys Val Glu Arg Ile Glu Lys Tyr Gln Asp Ser Phe Leu Leu Ala Phe
225                 230                 235                 240

Glu His Tyr Ile Asn Tyr Arg Lys His His Val Thr His Phe Trp Pro
                245                 250                 255

Lys Leu Leu Met Lys Val Thr Asp Leu Arg Met Ile Gly Ala Cys His
            260                 265                 270

Ala Ser Arg Phe Leu His Met Lys Val Glu Cys Pro Thr Glu Leu Phe
        275                 280                 285

Pro Pro Leu Phe Leu
        290

<210> SEQ ID NO 14
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Phe Gln Gly Leu Glu Asn Arg Thr Gln Gln Pro Ser Leu Thr Pro Leu
1               5                   10                  15

Ser Thr Ile Lys Ala Phe Ala Thr Gln Ser Gly Ser Gln Asp Leu Lys
            20                  25                  30

Ala Leu Asn Thr Thr Tyr Gln Ser Gln Leu Ile Lys Pro Ser Arg Met
        35                  40                  45

Arg Lys Tyr Pro Asn Arg Pro Ser Lys Thr Pro Pro His Glu Arg Pro
        50                  55                  60
```

Tyr
65

<210> SEQ ID NO 15
<211> LENGTH: 414
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Ala Ser Gly Asp Thr Leu Tyr Ile Ala Thr Asp Gly Ser Glu Met
1               5                   10                  15

Pro Ala Glu Ile Val Glu Leu His Glu Ile Glu Val Glu Thr Ile Pro
                20                  25                  30

Val Glu Thr Ile Glu Thr Thr Val Val Gly Glu Glu Glu Glu Glu Asp
                35                  40                  45

Asp Asp Asp Glu Asp Gly Gly Gly Asp His Gly Gly Gly Gly Gly Gly
        50                  55                  60

His Gly His Ala Gly His His His His His His His His His His
65                  70                  75                  80

Pro Pro Met Ile Ala Leu Gln Pro Leu Val Thr Asp Pro Thr Gln
                85                  90                  95

Val His His His Gln Glu Val Ile Leu Val Gln Thr Arg Glu Val
                100                 105                 110

Val Gly Gly Asp Asp Ser Asp Gly Leu Arg Ala Glu Asp Gly Phe Glu
            115                 120                 125

Asp Gln Ile Leu Ile Pro Val Pro Ala Pro Ala Gly Gly Asp Asp Asp
    130                 135                 140

Tyr Ile Glu Gln Thr Leu Val Thr Val Ala Ala Gly Lys Ser Gly
145                 150                 155                 160

Gly Gly Gly Ser Ser Ser Gly Gly Gly Arg Val Lys Lys Gly Gly
                165                 170                 175

Gly Lys Lys Ser Gly Lys Lys Ser Tyr Leu Ser Gly Gly Ala Gly Ala
                180                 185                 190

Ala Gly Gly Gly Ala Asp Pro Gly Asn Lys Lys Trp Glu Gln Lys
            195                 200                 205

Gln Val Gln Ile Lys Thr Leu Glu Gly Glu Phe Ser Val Thr Met Trp
    210                 215                 220

Ser Ser Asp Glu Lys Lys Asp Ile Asp His Glu Thr Val Val Glu Glu
225                 230                 235                 240

Gln Ile Ile Gly Glu Asn Ser Pro Pro Asp Tyr Ser Glu Tyr Met Thr
                245                 250                 255

Gly Lys Lys Leu Pro Pro Gly Gly Ile Pro Gly Ile Asp Leu Ser Asp
                260                 265                 270

Pro Lys Gln Leu Ala Glu Phe Ala Arg Met Lys Pro Arg Lys Ile Lys
            275                 280                 285

Glu Asp Asp Ala Pro Arg Thr Ile Ala Cys Pro His Lys Gly Cys Thr
    290                 295                 300

Lys Met Phe Arg Asp Asn Ser Ala Met Arg Lys His Leu His Thr His
305                 310                 315                 320

Gly Pro Arg Val His Val Cys Ala Glu Cys Gly Lys Ala Phe Val Glu
                325                 330                 335

Ser Ser Lys Leu Lys Arg His Gln Leu Val His Thr Gly Glu Lys Pro

```
              340                 345                 350

Phe Gln Cys Thr Phe Glu Gly Cys Gly Lys Arg Phe Ser Leu Asp Phe
            355                 360                 365

Asn Leu Arg Thr His Val Arg Ile His Thr Gly Asp Arg Pro Tyr Val
        370                 375                 380

Cys Pro Phe Asp Gly Cys Asn Lys Lys Phe Ala Gln Ser Thr Asn Leu
385                 390                 395                 400

Lys Ser His Ile Leu Thr His Ala Lys Ala Lys Asn Asn Gln
                405                 410

<210> SEQ ID NO 16
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gly Ser Ala Ser Ser His Ser Ser Ala Gly Tyr Glu Ser Ala Pro Gly
1               5                   10                  15

Ser Ser Ser Cys Ser Tyr Ala Pro Pro Ser Pro Ala Asn Ser Ser
            20                  25                  30

Tyr Glu Pro Met Asp Ile Lys Pro Ser Val Ile Gln Arg Val Pro Met
        35                  40                  45

Glu Gln Gln Pro Leu Ser Leu Val Ile Lys Lys Gln Ile Lys Glu Glu
    50                  55                  60

Glu Gln Pro Trp Arg Pro Trp
65                  70

<210> SEQ ID NO 17
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gly Gly Ala Ala Pro Pro Pro Gly Ser Ala Pro Cys Lys Leu Gly Ser
1               5                   10                  15

Gln Ala Gly Glu Ala Ala Lys Val Phe Gly Gly Phe Gln Val Val Pro
            20                  25                  30

Ala Pro Asp Gly Gln Phe Ala Phe Leu Ile Pro Asn Gly Ala Phe Ala
        35                  40                  45

His Ser Gly Pro Val Ile Pro Val Tyr Thr Ser Asn Ser Gly Thr Ser
    50                  55                  60

Val Gly Pro Asn Ala Val Ser Pro Ser Ser Gly Ser Ser Leu Thr Ala
65                  70                  75                  80

Asp Ser Met Trp Arg Pro Trp Arg Asn
                85

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18
```

```
Ser Gly Gly Gly Ser Gly Gly Ser Gly Ser
1               5                   10
```

<210> SEQ ID NO 19
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Gly Ser Ser Ser Ser Ser Thr Tyr Ser Ser Ala Ser Ser Cys Ser
1               5                   10                  15

Ser Ile Ser Pro Val Ser Ser Gly Tyr Ala Ser Asp Asn Glu Ser Leu
            20                  25                  30

Leu Gln Ile Ser Ser Pro Gly Gln Val Trp Arg Pro Trp
        35                  40                  45
```

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Trp Arg Pro Trp
1
```

<210> SEQ ID NO 21
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Arg Gln Gln Gln Ala Ala Ala Ala Ala Thr Ala Ala Met Met Leu
1               5                   10                  15

Glu Arg Ala Asn Phe Leu Asn Cys Phe Asn Pro Ala Ala Tyr Pro Arg
            20                  25                  30

Ile His Glu Glu Ile Val Gln Ser Arg Leu Arg Arg Ser Ala Ala Asn
        35                  40                  45

Ala Val Ile Pro Pro Pro Met
    50                  55
```

<210> SEQ ID NO 22
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

```
His Arg Ala Leu Pro Phe Ser Ile Asp Asn Ile Leu Ser Leu Asp Phe
1               5                   10                  15

Gly Arg Arg Lys Lys Val Ser
            20
```

<210> SEQ ID NO 23
<211> LENGTH: 770
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

Met Phe Pro Gln Ser Arg His Pro Thr Pro His Gln Ala Ala Gly Gln
1               5                   10                  15

Pro Phe Lys Phe Thr Ile Pro Glu Ser Leu Asp Arg Ile Lys Glu Glu
            20                  25                  30

Phe Gln Phe Leu Gln Ala Gln Tyr His Ser Leu Lys Leu Glu Cys Glu
        35                  40                  45

Lys Leu Ala Ser Glu Lys Thr Glu Met Gln Arg His Tyr Val Met Tyr
    50                  55                  60

Tyr Glu Met Ser Tyr Gly Leu Asn Ile Glu Met His Lys Gln Thr Glu
65                  70                  75                  80

Ile Ala Lys Arg Leu Asn Thr Ile Cys Ala Gln Val Ile Pro Phe Leu
                85                  90                  95

Ser Gln Glu His Gln Gln Val Ala Gln Ala Val Glu Arg Ala Lys
            100                 105                 110

Gln Val Thr Met Ala Glu Leu Asn Ala Ile Ile Gly Gln Gln Leu
        115                 120                 125

Gln Ala Gln His Leu Ser His Gly His Gly Pro Pro Val Pro Leu Thr
130                 135                 140

Pro His Pro Ser Gly Leu Gln Pro Pro Gly Ile Pro Pro Leu Gly Gly
145                 150                 155                 160

Ser Ala Gly Leu Leu Ala Leu Ser Ser Ala Leu Ser Gly Gln Ser His
                165                 170                 175

Leu Ala Ile Lys Asp Asp Lys Lys His His Asp Ala Glu His His Arg
            180                 185                 190

Asp Arg Glu Pro Gly Thr Ser Asn Ser Leu Leu Val Pro Asp Ser Leu
        195                 200                 205

Arg Gly Thr Asp Lys Arg Arg Asn Gly Pro Glu Phe Ser Asn Asp Ile
    210                 215                 220

Lys Lys Arg Lys Val Asp Asp Lys Asp Ser Ser His Tyr Asp Ser Asp
225                 230                 235                 240

Gly Asp Lys Ser Asp Asp Asn Leu Val Val Asp Val Ser Asn Glu Asp
                245                 250                 255

Pro Ser Ser Pro Arg Ala Ser Pro Ala His Ser Pro Arg Glu Asn Gly
            260                 265                 270

Ile Asp Lys Asn Arg Leu Leu Lys Lys Asp Ala Ser Ser Ser Pro Ala
        275                 280                 285

Ser Thr Ala Ser Ser Ala Ser Ser Thr Ser Leu Lys Ser Lys Glu Met
    290                 295                 300

Ser Leu His Glu Lys Ala Ser Thr Pro Val Leu Lys Ser Ser Thr Pro
305                 310                 315                 320

Thr Pro Arg Ser Asp Met Pro Thr Pro Gly Thr Ser Ala Thr Pro Gly
                325                 330                 335

Leu Arg Pro Gly Leu Gly Lys Pro Pro Ala Ile Asp Pro Leu Val Asn
            340                 345                 350

Gln Ala Ala Ala Gly Leu Arg Thr Pro Leu Ala Val Pro Gly Pro Tyr
        355                 360                 365

```
Pro Ala Pro Phe Gly Met Val Pro His Ala Gly Met Asn Gly Glu Leu
370                 375                 380

Thr Ser Pro Gly Ala Ala Tyr Ala Ser Leu His Asn Met Ser Pro Gln
385                 390                 395                 400

Met Ser Ala Ala Ala Ala Ala Ala Val Val Ala Tyr Gly Arg Ser
                405                 410                 415

Pro Met Val Gly Phe Asp Pro Pro His Met Arg Val Pro Thr Ile
        420                 425                 430

Pro Pro Asn Leu Ala Gly Ile Pro Gly Gly Lys Pro Ala Tyr Ser Phe
        435                 440                 445

His Val Thr Ala Asp Gly Gln Met Gln Pro Val Pro Phe Pro Asp
450                 455                 460

Ala Leu Ile Gly Pro Gly Ile Pro Arg His Ala Arg Gln Ile Asn Thr
465                 470                 475                 480

Leu Asn His Gly Glu Val Val Cys Ala Val Thr Ile Ser Asn Pro Thr
                485                 490                 495

Arg His Val Tyr Thr Gly Gly Lys Gly Cys Val Lys Val Trp Asp Ile
            500                 505                 510

Ser His Pro Gly Asn Lys Ser Pro Val Ser Gln Leu Asp Cys Leu Asn
        515                 520                 525

Arg Asp Asn Tyr Ile Arg Ser Cys Lys Leu Leu Pro Asp Gly Cys Thr
530                 535                 540

Leu Ile Val Gly Gly Glu Ala Ser Thr Leu Ser Ile Trp Asp Leu Ala
545                 550                 555                 560

Ala Pro Thr Pro Arg Ile Lys Ala Glu Leu Thr Ser Ser Ala Pro Ala
                565                 570                 575

Cys Tyr Ala Leu Ala Ile Ser Pro Asp Ser Lys Val Cys Phe Ser Cys
            580                 585                 590

Cys Ser Asp Gly Asn Ile Ala Val Trp Asp Leu His Asn Gln Thr Leu
    595                 600                 605

Val Arg Gln Phe Gln Gly His Thr Asp Gly Ala Ser Cys Ile Asp Ile
610                 615                 620

Ser Asn Asp Gly Thr Lys Leu Trp Thr Gly Gly Leu Asp Asn Thr Val
625                 630                 635                 640

Arg Ser Trp Asp Leu Arg Glu Gly Arg Gln Leu Gln Gln His Asp Phe
                645                 650                 655

Thr Ser Gln Ile Phe Ser Leu Gly Tyr Cys Pro Thr Gly Glu Trp Leu
            660                 665                 670

Ala Val Gly Met Glu Ser Ser Asn Val Glu Val Leu His Val Asn Lys
        675                 680                 685

Pro Asp Lys Tyr Gln Leu His Leu His Glu Ser Cys Val Leu Ser Leu
690                 695                 700

Lys Phe Ala Tyr Cys Gly Lys Trp Phe Val Ser Thr Gly Lys Asp Asn
705                 710                 715                 720

Leu Leu Asn Ala Trp Arg Thr Pro Tyr Gly Ala Ser Ile Phe Gln Ser
                725                 730                 735

Lys Glu Ser Ser Ser Val Leu Ser Cys Asp Ile Ser Val Asp Asp Lys
            740                 745                 750

Tyr Ile Val Thr Gly Ser Gly Asp Lys Lys Ala Thr Val Tyr Glu Val
        755                 760                 765

Ile Tyr
770
```

```
<210> SEQ ID NO 24
<211> LENGTH: 743
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Tyr Pro Gln Gly Arg His Pro Thr Pro Leu Gln Ser Gly Gln Pro
1               5                   10                  15

Phe Lys Phe Ser Ile Leu Glu Ile Cys Asp Arg Ile Lys Glu Glu Phe
            20                  25                  30

Gln Phe Leu Gln Ala Gln Tyr His Ser Leu Lys Leu Glu Cys Glu Lys
        35                  40                  45

Leu Ala Ser Glu Lys Thr Glu Met Gln Arg His Tyr Val Met Tyr Tyr
    50                  55                  60

Glu Met Ser Tyr Gly Leu Asn Ile Glu Met His Lys Gln Ala Glu Ile
65                  70                  75                  80

Val Lys Arg Leu Ser Gly Ile Cys Ala Gln Ile Ile Pro Phe Leu Thr
                85                  90                  95

Gln Glu His Gln Gln Val Leu Gln Ala Val Glu Arg Ala Lys Gln
            100                 105                 110

Val Thr Val Gly Glu Leu Asn Ser Leu Ile Gly Gln Gln Leu Gln Pro
        115                 120                 125

Leu Ser His His Ala Pro Pro Val Pro Leu Thr Pro Arg Pro Ala Gly
    130                 135                 140

Leu Val Gly Gly Ser Ala Thr Gly Leu Leu Ala Leu Ser Gly Ala Leu
145                 150                 155                 160

Ala Ala Gln Ala Gln Leu Ala Ala Ala Val Lys Glu Asp Arg Ala Gly
                165                 170                 175

Val Glu Ala Glu Gly Ser Arg Val Glu Arg Ala Pro Ser Arg Ser Ala
            180                 185                 190

Ser Pro Ser Pro Pro Glu Ser Leu Val Glu Glu Arg Pro Ser Gly
        195                 200                 205

Pro Gly Gly Gly Lys Gln Arg Ala Asp Glu Lys Glu Pro Ser Gly
    210                 215                 220

Pro Tyr Glu Ser Asp Glu Asp Lys Ser Asp Tyr Asn Leu Val Val Asp
225                 230                 235                 240

Glu Asp Gln Pro Ser Glu Pro Pro Ser Pro Ala Thr Thr Pro Cys Gly
                245                 250                 255

Lys Val Pro Ile Cys Ile Pro Ala Arg Arg Asp Leu Val Asp Ser Pro
            260                 265                 270

Ala Ser Leu Ala Ser Ser Leu Gly Ser Pro Leu Pro Arg Ala Lys Glu
        275                 280                 285

Leu Ile Leu Asn Asp Leu Pro Ala Ser Thr Pro Ala Ser Lys Ser Cys
    290                 295                 300

Asp Ser Ser Pro Pro Gln Asp Ala Ser Thr Pro Gly Pro Ser Ser Ala
305                 310                 315                 320

Ser His Leu Cys Gln Leu Ala Ala Lys Pro Ala Pro Ser Thr Asp Ser
                325                 330                 335

Val Ala Leu Arg Ser Pro Leu Thr Leu Ser Ser Pro Phe Thr Thr Ser
            340                 345                 350

Phe Ser Leu Gly Ser His Ser Thr Leu Asn Gly Asp Leu Ser Val Pro
        355                 360                 365
```

```
Ser Ser Tyr Val Ser Leu His Leu Ser Pro Gln Val Ser Ser Val
370                 375                 380

Val Tyr Gly Arg Ser Pro Val Met Ala Phe Glu Ser His Pro His Leu
385                 390                 395                 400

Arg Gly Ser Ser Val Ser Ser Leu Pro Ser Ile Pro Gly Gly Lys
            405                 410                 415

Pro Ala Tyr Ser Phe His Val Ser Ala Asp Gly Gln Met Gln Pro Val
            420                 425                 430

Pro Phe Pro Ser Asp Ala Leu Val Gly Ala Gly Ile Pro Arg His Ala
            435                 440                 445

Arg Gln Leu His Thr Leu Ala His Gly Glu Val Val Cys Ala Val Thr
450                 455                 460

Ile Ser Gly Ser Thr Gln His Val Tyr Thr Gly Gly Lys Gly Cys Val
465                 470                 475                 480

Lys Val Trp Asp Val Gly Gln Pro Gly Ala Lys Thr Pro Val Ala Gln
                485                 490                 495

Leu Asp Cys Leu Asn Arg Asp Asn Tyr Ile Arg Ser Cys Lys Leu Leu
            500                 505                 510

Pro Asp Gly Arg Ser Leu Ile Val Gly Gly Glu Ala Ser Thr Leu Ser
            515                 520                 525

Ile Trp Asp Leu Ala Ala Pro Thr Pro Arg Ile Lys Ala Glu Leu Thr
530                 535                 540

Ser Ser Ala Pro Ala Cys Tyr Ala Leu Ala Val Ser Pro Asp Ala Lys
545                 550                 555                 560

Val Cys Phe Ser Cys Cys Ser Asp Gly Asn Ile Val Val Trp Asp Leu
                565                 570                 575

Gln Asn Gln Thr Met Val Arg Gln Phe Gln Gly His Thr Asp Gly Ala
            580                 585                 590

Ser Cys Ile Asp Ile Ser Asp Tyr Gly Thr Arg Leu Trp Thr Gly Gly
            595                 600                 605

Leu Asp Asn Thr Val Arg Cys Trp Asp Leu Arg Glu Gly Arg Gln Leu
610                 615                 620

Gln Gln His Asp Phe Ser Ser Gln Ile Phe Ser Leu Gly His Cys Pro
625                 630                 635                 640

Asn Gln Asp Trp Leu Ala Val Gly Met Glu Ser Ser Asn Val Glu Ile
                645                 650                 655

Leu His Val Arg Lys Pro Glu Lys Tyr Gln Leu His Leu His Glu Ser
            660                 665                 670

Cys Val Leu Ser Leu Lys Phe Ala Ser Cys Gly Arg Trp Phe Val Ser
            675                 680                 685

Thr Gly Lys Asp Asn Leu Leu Asn Ala Trp Arg Thr Pro Tyr Gly Ala
690                 695                 700

Ser Ile Phe Gln Ser Lys Glu Ser Ser Val Leu Ser Cys Asp Ile
705                 710                 715                 720

Ser Arg Asn Asn Lys Tyr Ile Val Thr Gly Ser Gly Asp Lys Lys Ala
                725                 730                 735

Thr Val Tyr Glu Val Val Tyr
            740

<210> SEQ ID NO 25
<211> LENGTH: 772
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 25

```
Met Tyr Pro Gln Gly Arg His Pro Ala Pro His Gln Pro Gly Gln Pro
1               5                   10                  15

Gly Phe Lys Phe Thr Val Ala Glu Ser Cys Asp Arg Ile Lys Asp Glu
            20                  25                  30

Phe Gln Phe Leu Gln Ala Gln Tyr His Ser Leu Lys Val Glu Tyr Asp
        35                  40                  45

Lys Leu Ala Asn Glu Lys Thr Glu Met Gln Arg His Tyr Val Met Tyr
    50                  55                  60

Tyr Glu Met Ser Tyr Gly Leu Asn Ile Glu Met His Lys Gln Thr Glu
65                  70                  75                  80

Ile Ala Lys Arg Leu Asn Thr Ile Leu Ala Gln Ile Met Pro Phe Leu
                85                  90                  95

Ser Gln Glu His Gln Gln Val Ala Gln Ala Val Glu Arg Ala Lys
            100                 105                 110

Gln Val Thr Met Thr Glu Leu Asn Ala Ile Ile Gly Gln Gln Gln Leu
            115                 120                 125

Gln Ala Gln His Leu Ser His Ala Thr His Gly Pro Pro Val Gln Leu
    130                 135                 140

Pro His Pro Ser Gly Leu Gln Pro Pro Gly Ile Pro Pro Val Thr
145                 150                 155                 160

Gly Ser Ser Ser Gly Leu Leu Ala Leu Gly Ala Leu Gly Ser Gln Ala
                165                 170                 175

His Leu Thr Val Lys Asp Glu Lys Asn His His Glu Leu Asp His Arg
            180                 185                 190

Glu Arg Glu Ser Ser Ala Asn Asn Ser Val Ser Pro Ser Glu Ser Leu
        195                 200                 205

Arg Ala Ser Glu Lys His Arg Gly Ser Ala Asp Tyr Ser Met Glu Ala
    210                 215                 220

Lys Lys Arg Lys Ala Glu Glu Lys Asp Ser Leu Ser Arg Tyr Asp Ser
225                 230                 235                 240

Asp Gly Asp Lys Ser Asp Leu Val Val Asp Val Ser Asn Glu Asp
                245                 250                 255

Pro Ala Thr Pro Arg Val Ser Pro Ala His Ser Pro Glu Asn Gly
            260                 265                 270

Leu Asp Lys Ala Arg Ser Leu Lys Lys Asp Ala Pro Thr Ser Pro Ala
    275                 280                 285

Ser Val Ala Ser Ser Ser Thr Pro Ser Ser Lys Thr Lys Asp Leu
290                 295                 300

Gly His Asn Asp Lys Ser Ser Thr Pro Gly Leu Lys Ser Asn Thr Pro
305                 310                 315                 320

Thr Pro Arg Asn Asp Ala Pro Thr Pro Gly Thr Ser Thr Thr Pro Gly
                325                 330                 335

Leu Arg Ser Met Pro Gly Lys Pro Pro Gly Met Asp Pro Ile Gly Ile
            340                 345                 350

Met Ala Ser Ala Leu Arg Thr Pro Ile Ser Ile Thr Ser Ser Tyr Ala
        355                 360                 365

Ala Pro Phe Ala Met Met Ser His His Glu Met Asn Gly Ser Leu Thr
    370                 375                 380

Ser Pro Gly Ala Tyr Ala Gly Leu His Asn Ile Pro Pro Gln Met Ser
385                 390                 395                 400
```

Ala Ala Ala Ala Ala Ala Ala Tyr Gly Arg Ser Pro Met Val
                405                 410                 415

Ser Phe Gly Ala Val Gly Phe Asp Pro His Pro Met Arg Ala Thr
            420                 425                 430

Gly Leu Pro Ser Ser Leu Ala Ser Ile Pro Gly Gly Lys Pro Ala Tyr
        435                 440                 445

Ser Phe His Val Ser Ala Asp Gly Gln Met Gln Pro Val Pro Phe Pro
    450                 455                 460

His Asp Ala Leu Ala Gly Pro Gly Ile Pro Arg His Ala Arg Gln Ile
465                 470                 475                 480

Asn Thr Leu Ser His Gly Glu Val Val Cys Ala Val Thr Ile Ser Asn
                485                 490                 495

Pro Thr Arg His Val Tyr Thr Gly Gly Lys Gly Cys Val Lys Ile Trp
            500                 505                 510

Asp Ile Ser Gln Pro Gly Ser Lys Ser Pro Ile Ser Gln Leu Asp Cys
        515                 520                 525

Leu Asn Arg Asp Asn Tyr Ile Arg Ser Cys Lys Leu Leu Pro Asp Gly
    530                 535                 540

Arg Thr Leu Ile Val Gly Gly Glu Ala Ser Thr Leu Thr Ile Trp Asp
545                 550                 555                 560

Leu Ala Ser Pro Thr Pro Arg Ile Lys Ala Glu Leu Thr Ser Ser Ala
                565                 570                 575

Pro Ala Cys Tyr Ala Leu Ala Ile Ser Pro Asp Ala Lys Val Cys Phe
            580                 585                 590

Ser Cys Cys Ser Asp Gly Asn Ile Ala Val Trp Asp Leu His Asn Gln
        595                 600                 605

Thr Leu Val Arg Gln Phe Gln Gly His Thr Asp Gly Ala Ser Cys Ile
    610                 615                 620

Asp Ile Ser His Asp Gly Thr Lys Leu Trp Thr Gly Leu Asp Asn
625                 630                 635                 640

Thr Val Arg Ser Trp Asp Leu Arg Glu Gly Arg Gln Leu Gln Gln His
                645                 650                 655

Asp Phe Thr Ser Gln Ile Phe Ser Leu Gly Tyr Cys Pro Thr Gly Glu
            660                 665                 670

Trp Leu Ala Val Gly Met Glu Ser Ser Asn Val Glu Val Leu His His
        675                 680                 685

Thr Lys Pro Asp Lys Tyr Gln Leu His Leu His Glu Ser Cys Val Leu
    690                 695                 700

Ser Leu Lys Phe Ala Tyr Cys Gly Lys Trp Phe Val Ser Thr Gly Lys
705                 710                 715                 720

Asp Asn Leu Leu Asn Ala Trp Arg Thr Pro Tyr Gly Ala Ser Ile Phe
                725                 730                 735

Gln Ser Lys Glu Ser Ser Ser Val Leu Ser Cys Asp Ile Ser Ala Asp
            740                 745                 750

Asp Lys Tyr Ile Val Thr Gly Ser Gly Asp Lys Lys Ala Thr Val Tyr
        755                 760                 765

Glu Val Ile Tyr
770

<210> SEQ ID NO 26
<211> LENGTH: 773
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

```
Met Ile Arg Asp Leu Ser Lys Met Tyr Pro Gln Thr Arg His Pro Ala
1               5                   10                  15

Pro His Gln Pro Ala Gln Pro Phe Lys Phe Thr Ile Ser Glu Ser Cys
            20                  25                  30

Asp Arg Ile Lys Glu Glu Phe Gln Phe Leu Gln Ala Gln Tyr His Ser
        35                  40                  45

Leu Lys Leu Glu Cys Glu Lys Leu Ala Ser Glu Lys Thr Glu Met Gln
    50                  55                  60

Arg His Tyr Val Met Tyr Tyr Glu Met Ser Tyr Gly Leu Asn Ile Glu
65                  70                  75                  80

Met His Lys Gln Ala Glu Ile Val Lys Arg Leu Asn Ala Ile Cys Ala
                85                  90                  95

Gln Val Ile Pro Phe Leu Ser Gln Glu His Gln Gln Gln Val Val Gln
            100                 105                 110

Ala Val Glu Arg Ala Lys Gln Val Thr Met Ala Glu Leu Asn Ala Ile
        115                 120                 125

Ile Gly Gln Gln Leu Gln Ala Gln His Leu Ser His Gly His Gly Leu
    130                 135                 140

Pro Val Pro Leu Thr Pro His Pro Ser Gly Leu Gln Pro Pro Ala Ile
145                 150                 155                 160

Pro Pro Ile Gly Ser Ser Ala Gly Leu Leu Ala Leu Ser Ser Ala Leu
                165                 170                 175

Gly Gly Gln Ser His Leu Pro Ile Lys Asp Glu Lys Lys His His Asp
            180                 185                 190

Asn Asp His Gln Arg Asp Arg Asp Ser Ile Lys Ser Ser Ser Val Ser
        195                 200                 205

Pro Ser Ala Ser Phe Arg Gly Ala Glu Lys His Arg Asn Ser Ala Asp
    210                 215                 220

Tyr Ser Ser Glu Ser Lys Lys Gln Lys Thr Glu Glu Lys Glu Ile Ala
225                 230                 235                 240

Ala Arg Tyr Asp Ser Asp Gly Glu Lys Ser Asp Asp Asn Leu Val Val
                245                 250                 255

Asp Val Ser Asn Glu Asp Pro Ser Ser Pro Arg Gly Ser Pro Ala His
            260                 265                 270

Ser Pro Arg Glu Asn Gly Leu Asp Lys Thr Arg Leu Leu Lys Lys Asp
        275                 280                 285

Ala Pro Ile Ser Pro Ala Ser Ile Ala Ser Ser Ser Ser Thr Pro Ser
    290                 295                 300

Ser Lys Ser Lys Glu Leu Ser Leu Asn Glu Lys Ser Thr Thr Pro Val
305                 310                 315                 320

Ser Lys Ser Asn Thr Pro Thr Pro Arg Thr Asp Ala Pro Thr Pro Gly
                325                 330                 335

Ser Asn Ser Thr Pro Gly Leu Arg Pro Val Pro Gly Lys Pro Pro Gly
            340                 345                 350

Val Asp Pro Leu Ala Ser Ser Leu Arg Thr Pro Met Ala Val Pro Cys
        355                 360                 365

Pro Tyr Pro Thr Pro Phe Gly Ile Val Pro His Ala Gly Met Asn Gly
    370                 375                 380

Glu Leu Thr Ser Pro Gly Ala Ala Tyr Ala Gly Leu His Asn Ile Ser
385                 390                 395                 400
```

Pro Gln Met Ser Ala Ala Ala Ala Ala Ala Ala Ala Tyr
            405                 410                 415

Gly Arg Ser Pro Val Val Gly Phe Asp Pro His His Met Arg Val
        420                 425                 430

Pro Ala Ile Pro Pro Asn Leu Thr Gly Ile Pro Gly Gly Lys Pro Ala
            435                 440                 445

Tyr Ser Phe His Val Ser Ala Asp Gly Gln Met Gln Pro Val Pro Phe
        450                 455                 460

Pro Pro Asp Ala Leu Ile Gly Pro Gly Ile Pro Arg His Ala Arg Gln
465                 470                 475                 480

Ile Asn Thr Leu Asn His Gly Glu Val Val Cys Ala Val Thr Ile Ser
                485                 490                 495

Asn Pro Thr Arg His Val Tyr Thr Gly Gly Lys Gly Cys Val Lys Val
            500                 505                 510

Trp Asp Ile Ser His Pro Gly Asn Lys Ser Pro Val Ser Gln Leu Asp
        515                 520                 525

Cys Leu Asn Arg Asp Asn Tyr Ile Arg Ser Cys Arg Leu Leu Pro Asp
530                 535                 540

Gly Arg Thr Leu Ile Val Gly Gly Glu Ala Ser Thr Leu Ser Ile Trp
545                 550                 555                 560

Asp Leu Ala Ala Pro Thr Pro Arg Ile Lys Ala Glu Leu Thr Ser Ser
                565                 570                 575

Ala Pro Ala Cys Tyr Ala Leu Ala Ile Ser Pro Asp Ser Lys Val Cys
            580                 585                 590

Phe Ser Cys Cys Ser Asp Gly Asn Ile Ala Val Trp Asp Leu His Asn
        595                 600                 605

Gln Thr Leu Val Arg Gln Phe Gln Gly His Thr Asp Gly Ala Ser Cys
610                 615                 620

Ile Asp Ile Ser Asn Asp Gly Thr Lys Leu Trp Thr Gly Gly Leu Asp
625                 630                 635                 640

Asn Thr Val Arg Ser Trp Asp Leu Arg Glu Gly Arg Gln Leu Gln Gln
                645                 650                 655

His Asp Phe Thr Ser Gln Ile Phe Ser Leu Gly Tyr Cys Pro Thr Gly
            660                 665                 670

Glu Trp Leu Ala Val Gly Met Glu Asn Ser Asn Val Glu Val Leu His
        675                 680                 685

Val Thr Lys Pro Asp Lys Tyr Gln Leu His Leu His Glu Ser Cys Val
        690                 695                 700

Leu Ser Leu Lys Phe Ala His Cys Gly Lys Trp Phe Val Ser Thr Gly
705                 710                 715                 720

Lys Asp Asn Leu Leu Asn Ala Trp Arg Thr Pro Tyr Gly Ala Ser Ile
                725                 730                 735

Phe Gln Ser Lys Glu Ser Ser Val Leu Ser Cys Asp Ile Ser Val
            740                 745                 750

Asp Asp Lys Tyr Ile Val Thr Gly Ser Gly Asp Lys Lys Ala Thr Val
        755                 760                 765

Tyr Glu Val Ile Tyr
        770

<210> SEQ ID NO 27
<211> LENGTH: 488
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

```
Met Ala Tyr Ser Gln Gly Gly Lys Lys Val Cys Tyr Tyr
1               5                   10                  15

Asp Gly Asp Ile Gly Asn Tyr Tyr Gly Gln Gly His Pro Met Lys
            20                  25                  30

Pro His Arg Ile Arg Met Thr His Asn Leu Leu Asn Tyr Gly Leu
        35                  40                  45

Tyr Arg Lys Met Glu Ile Tyr Arg Pro His Lys Ala Thr Ala Glu
    50                  55                  60

Met Thr Lys Tyr His Ser Asp Glu Tyr Ile Lys Phe Leu Arg Ser Ile
65                  70                  75                  80

Arg Pro Asp Asn Met Ser Glu Tyr Ser Lys Gln Met Gln Arg Phe Asn
                85                  90                  95

Val Gly Glu Asp Cys Pro Val Phe Asp Gly Leu Phe Glu Phe Cys Gln
            100                 105                 110

Leu Ser Thr Gly Gly Ser Val Ala Gly Ala Val Lys Leu Asn Arg Gln
            115                 120                 125

Gln Thr Asp Met Ala Val Asn Trp Ala Gly Gly Leu His His Ala Lys
    130                 135                 140

Lys Ser Glu Ala Ser Gly Phe Cys Tyr Val Asn Asp Ile Val Leu Ala
145                 150                 155                 160

Ile Leu Glu Leu Leu Lys Tyr His Gln Arg Val Leu Tyr Ile Asp Ile
                165                 170                 175

Asp Ile His His Gly Asp Gly Val Glu Glu Ala Phe Tyr Thr Thr Asp
            180                 185                 190

Arg Val Met Thr Val Ser Phe His Lys Tyr Gly Glu Tyr Phe Pro Gly
        195                 200                 205

Thr Gly Asp Leu Arg Asp Ile Gly Ala Gly Lys Gly Lys Tyr Tyr Ala
    210                 215                 220

Val Asn Phe Pro Met Arg Asp Gly Ile Asp Asp Glu Ser Tyr Gly Gln
225                 230                 235                 240

Ile Phe Lys Pro Ile Ile Ser Lys Val Met Glu Met Tyr Gln Pro Ser
                245                 250                 255

Ala Val Val Leu Gln Cys Gly Ala Asp Ser Leu Ser Gly Asp Arg Leu
            260                 265                 270

Gly Cys Phe Asn Leu Thr Val Lys Gly His Ala Lys Cys Val Glu Val
        275                 280                 285

Val Lys Thr Phe Asn Leu Pro Leu Leu Met Leu Gly Gly Gly Gly Tyr
    290                 295                 300

Thr Ile Arg Asn Val Ala Arg Cys Trp Thr Tyr Glu Thr Ala Val Ala
305                 310                 315                 320

Leu Asp Cys Glu Ile Pro Asn Glu Leu Pro Tyr Asn Asp Tyr Phe Glu
                325                 330                 335

Tyr Phe Gly Pro Asp Phe Lys Leu His Ile Ser Pro Ser Asn Met Thr
            340                 345                 350

Asn Gln Asn Thr Pro Glu Tyr Met Glu Lys Ile Lys Gln Arg Leu Phe
        355                 360                 365

Glu Asn Leu Arg Met Leu Pro His Ala Pro Gly Val Gln Met Gln Ala
    370                 375                 380

Ile Pro Glu Asp Ala Val His Glu Asp Ser Gly Asp Glu Asp Gly Glu
385                 390                 395                 400
```

```
Asp Pro Asp Lys Arg Ile Ser Ile Arg Ala Ser Asp Lys Arg Ile Ala
                405                 410                 415

Cys Asp Glu Glu Phe Ser Asp Ser Glu Asp Glu Gly Glu Gly Gly Arg
            420                 425                 430

Arg Asn Val Ala Asp His Lys Lys Gly Ala Lys Lys Ala Arg Ile Glu
            435                 440                 445

Glu Asp Lys Lys Glu Thr Glu Asp Lys Lys Thr Asp Val Lys Glu Glu
        450                 455                 460

Asp Lys Ser Lys Asp Asn Ser Gly Glu Lys Thr Asp Thr Lys Gly Thr
465                 470                 475                 480

Lys Ser Glu Gln Leu Ser Asn Pro
                485

<210> SEQ ID NO 28
<211> LENGTH: 747
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Ala Asp Glu Ala Ala Leu Ala Leu Gln Pro Gly Gly Ser Pro Ser
1               5                   10                  15

Ala Ala Gly Ala Asp Arg Glu Ala Ala Ser Ser Pro Ala Gly Glu Pro
            20                  25                  30

Leu Arg Lys Arg Pro Arg Arg Asp Gly Pro Gly Leu Glu Arg Ser Pro
        35                  40                  45

Gly Glu Pro Gly Gly Ala Ala Pro Glu Arg Glu Val Pro Ala Ala Ala
    50                  55                  60

Arg Gly Cys Pro Gly Ala Ala Ala Ala Leu Trp Arg Glu Ala Glu
65                  70                  75                  80

Ala Glu Ala Ala Ala Gly Gly Glu Gln Glu Ala Gln Ala Thr Ala
                85                  90                  95

Ala Ala Gly Glu Gly Asp Asn Gly Pro Gly Leu Gln Gly Pro Ser Arg
            100                 105                 110

Glu Pro Pro Leu Ala Asp Asn Leu Tyr Asp Glu Asp Asp Asp Asp Glu
        115                 120                 125

Gly Glu Glu Glu Glu Ala Ala Ala Ala Ile Gly Tyr Arg Asp
    130                 135                 140

Asn Leu Leu Phe Gly Asp Glu Ile Ile Thr Asn Gly Phe His Ser Cys
145                 150                 155                 160

Glu Ser Asp Glu Glu Asp Arg Ala Ser His Ala Ser Ser Ser Asp Trp
                165                 170                 175

Thr Pro Arg Pro Arg Ile Gly Pro Tyr Thr Phe Val Gln Gln His Leu
            180                 185                 190

Met Ile Gly Thr Asp Pro Arg Thr Ile Leu Lys Asp Leu Leu Pro Glu
        195                 200                 205

Thr Ile Pro Pro Pro Glu Leu Asp Asp Met Thr Leu Trp Gln Ile Val
    210                 215                 220

Ile Asn Ile Leu Ser Glu Pro Pro Lys Arg Lys Lys Arg Lys Asp Ile
225                 230                 235                 240

Asn Thr Ile Glu Asp Ala Val Lys Leu Leu Gln Glu Cys Lys Lys Ile
                245                 250                 255

Ile Val Leu Thr Gly Ala Gly Val Ser Val Ser Cys Gly Ile Pro Asp
            260                 265                 270
```

-continued

```
Phe Arg Ser Arg Asp Gly Ile Tyr Ala Arg Leu Ala Val Asp Phe Pro
            275                 280                 285
Asp Leu Pro Asp Pro Gln Ala Met Phe Asp Ile Glu Tyr Phe Arg Lys
290                 295                 300
Asp Pro Arg Pro Phe Phe Lys Phe Ala Lys Glu Ile Tyr Pro Gly Gln
305                 310                 315                 320
Phe Gln Pro Ser Leu Cys His Lys Phe Ile Ala Leu Ser Asp Lys Glu
                325                 330                 335
Gly Lys Leu Leu Arg Asn Tyr Thr Gln Asn Ile Asp Thr Leu Glu Gln
                340                 345                 350
Val Ala Gly Ile Gln Arg Ile Ile Gln Cys His Gly Ser Phe Ala Thr
            355                 360                 365
Ala Ser Cys Leu Ile Cys Lys Tyr Lys Val Asp Cys Glu Ala Val Arg
        370                 375                 380
Gly Asp Ile Phe Asn Gln Val Val Pro Arg Cys Pro Arg Cys Pro Ala
385                 390                 395                 400
Asp Glu Pro Leu Ala Ile Met Lys Pro Glu Ile Val Phe Phe Gly Glu
                405                 410                 415
Asn Leu Pro Glu Gln Phe His Arg Ala Met Lys Tyr Asp Lys Asp Glu
            420                 425                 430
Val Asp Leu Leu Ile Val Ile Gly Ser Ser Leu Lys Val Arg Pro Val
        435                 440                 445
Ala Leu Ile Pro Ser Ser Ile Pro His Glu Val Pro Gln Ile Leu Ile
    450                 455                 460
Asn Arg Glu Pro Leu Pro His Leu His Phe Asp Val Glu Leu Leu Gly
465                 470                 475                 480
Asp Cys Asp Val Ile Ile Asn Glu Leu Cys His Arg Leu Gly Gly Glu
                485                 490                 495
Tyr Ala Lys Leu Cys Cys Asn Pro Val Lys Leu Ser Glu Ile Thr Glu
            500                 505                 510
Lys Pro Pro Arg Thr Gln Lys Glu Leu Ala Tyr Leu Ser Glu Leu Pro
        515                 520                 525
Pro Thr Pro Leu His Val Ser Glu Asp Ser Ser Pro Glu Arg Thr
    530                 535                 540
Ser Pro Pro Asp Ser Ser Val Ile Val Thr Leu Leu Asp Gln Ala Ala
545                 550                 555                 560
Lys Ser Asn Asp Asp Leu Asp Val Ser Glu Ser Lys Gly Cys Met Glu
                565                 570                 575
Glu Lys Pro Gln Glu Val Gln Thr Ser Arg Asn Val Glu Ser Ile Ala
            580                 585                 590
Glu Gln Met Glu Asn Pro Asp Leu Lys Asn Val Gly Ser Ser Thr Gly
        595                 600                 605
Glu Lys Asn Glu Arg Thr Ser Val Ala Gly Thr Val Arg Lys Cys Trp
    610                 615                 620
Pro Asn Arg Val Ala Lys Glu Gln Ile Ser Arg Arg Leu Asp Gly Asn
625                 630                 635                 640
Gln Tyr Leu Phe Leu Pro Pro Asn Arg Tyr Ile Phe His Gly Ala Glu
                645                 650                 655
Val Tyr Ser Asp Ser Glu Asp Asp Val Leu Ser Ser Ser Ser Cys Gly
            660                 665                 670
Ser Asn Ser Asp Ser Gly Thr Cys Gln Ser Pro Ser Leu Glu Glu Pro
        675                 680                 685
```

Met Glu Asp Glu Ser Glu Ile Glu Glu Phe Tyr Asn Gly Leu Glu Asp
690             695                 700
Glu Pro Asp Val Pro Glu Arg Ala Gly Ala Gly Phe Gly Thr Asp
705             710                 715                 720
Gly Asp Asp Gln Glu Ala Ile Asn Glu Ala Ile Ser Val Lys Gln Glu
                725                 730                 735
Val Thr Asp Met Asn Tyr Pro Ser Asn Lys Ser
            740                 745

<210> SEQ ID NO 29
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Thr Glu Glu Asn Val Lys Arg Arg Thr His Asn Val Leu Glu Arg
1               5                   10                  15
Gln Arg Arg Asn Glu Leu Lys Arg Ser Phe Phe Ala Leu Arg Asp Gln
                20                  25                  30
Ile Pro Glu Leu Glu Asn Asn Glu Lys Ala Pro Lys Val Val Ile Leu
            35                  40                  45
Lys Lys Ala Thr Ala Tyr Ile Leu Ser Val Gln Ala Glu Thr Gln Lys
50                  55                  60
Leu Ile Ser Glu Ile Asp Leu Leu Arg Lys Gln Asn Glu Gln Leu Lys
65                  70                  75                  80
His Lys Leu Glu Gln Leu Arg Asn Ser Cys Ala Ser Gly Gly Gly Ser
                85                  90                  95
Gly Gly Ser Gly Ser Met Asp Ala Lys Ser Leu Thr Ala Trp Ser Arg
            100                 105                 110
Thr Leu Val Thr Phe Lys Asp Val Phe Val Asp Phe Thr Arg Glu Glu
            115                 120                 125
Trp Lys Leu Leu Asp Thr Ala Gln Gln Ile Val Tyr Arg Asn Val Met
130                 135                 140
Leu Glu Asn Tyr Lys Asn Leu Val Ser Leu Gly Tyr Gln Leu Thr Lys
145                 150                 155                 160
Pro Asp Val Ile Leu Arg Leu Glu Lys Gly Glu Glu Pro Trp Leu Val
                165                 170                 175
Glu Arg Glu Ile His Gln Glu Thr His Pro Asp Ser Gly Thr Ala Phe
            180                 185                 190
Glu Ile Lys Ser Ser Val
            195

<210> SEQ ID NO 30
<211> LENGTH: 463
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
taacttgttc tttttgcaga agctcagaat aaacgctcaa ctttggccac catgaccgag     60
gagaatgtca agaggcgaac acacaacgtc ttggagcgcc agaggaggaa cgagctaaaa    120
cggagctttt ttgccctgcg tgaccagatc ccggagttgg aaaacaatga aaaggccccc    180
aaggtagtta tccttaaaaa agccacagca tacatcctgt ccgtccaagc agagacgcaa     240
aagctcattt ctgaaatcga cttgttgcgg aaacaaaacg aacagttgaa acacaaactt     300
gaacagctac ggaactcttg tgcgtaatga tagaccagcc tcaagaacac ccgaatggag     360
tctctaagct acataatacc aacttacact ttacaaaatg ttgtccccca aaatgtagcc     420
attcgtatct gctcctaata aaaagaaagt ttcttcacat tct                       463

```
<210> SEQ ID NO 31
<211> LENGTH: 784
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
```
taacttgttc tttttgcaga agctcagaat aaacgctcaa ctttggccac catgaccgag      60
gagaatgtca agaggcgaac acacaacgtc ttggagcgcc agaggaggaa cgagctaaaa     120
cggagctttt ttgccctgcg tgaccagatc ccggagttgg aaaacaatga aaaggccccc     180
aaggtagtta tccttaaaaa agccacagca tacatcctgt ccgtccaagc agagacgcaa     240
aagctcattt ctgaaatcga cttgttgcgg aaacaaaacg aacagttgaa acacaaactt     300
gaacagctac ggaactcttg tgcgagcggt ggaggaagcg gcggatctgg atccatggat     360
gctaagtcac taactgcctg gtcccggaca ctggtgacct tcaaggatgt atttgtggac     420
ttcaccaggg aggagtggaa gctgctggac actgctcagc agatcgtgta cagaaatgtg     480
atgctggaga actataagaa cctggttttc cttgggttatc agcttactaa gccagatgtg     540
atcctccggt tggagaaggg agaagagccc tggctggtgg agagagaaat tcaccaagag     600
acccatcctg attcagagac tgcatttgaa atcaaatcat cagtttaatg atagaccagc     660
ctcaagaaca cccgaatgga gtctctaagc tacataatac caacttacac tttacaaaat     720
gttgtccccc aaaatgtagc cattcgtatc tgctcctaat aaaaagaaag tttcttcaca     780
ttct                                                                  784

```
<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
```
caccatgggc gtgatcaagc ccgacatg                                         28

```
<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
```
ttagccggcc tggcggggta gt                                               22

```
<210> SEQ ID NO 34
<211> LENGTH: 28
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 34
caccatgacc gaggagaatg tcaagagg                                           28

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ttacgcacaa gagttccgta gctgttcaag                                         30

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
caccatgacc gaggagaatg                                                    20

<210> SEQ ID NO 37
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ttaaactgat gatttgattt caaatgcagt c                                       31

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
taatacgact cactataggg                                                    20

<210> SEQ ID NO 39
<211> LENGTH: 358
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
caccatgcct gcagcaaaac gggtgaaact tgatggcggg gggggttctg gtggaggagg        60
aagcggtgga ggtgggtcta ccgaggagaa tgtcaagagg cgaacacaca acgtcttgga       120
gcgccagagg aggaacgagc tgaaacggag ctttttgcc ctgagagacc agatcccgga        180
gttggaaaac aatgaaaagg ccccccaagt agttatcctt aaaaaagcca cagcatacat       240
```

```
cctgtccgtc caagcagaga cgcaaaagct catttctgaa atcgacttgt tgcggaaaca        300
aaacgaacag ttgaaacaca aacttgaaca gctgcggaac tcttgtgcgt aatgatag         358
```

<210> SEQ ID NO 40
<211> LENGTH: 358
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 40

```
caccatgacc gaggagaatg tcaagaggcg aacacacaac gtcttggagc gccagaggag        60
gaacgagctg aaacggagct tttttgccct gagagaccag atcccggagt tggaaaacaa       120
tgaaaaggcc cccaaggtag ttatccttaa aaaagccaca gcatacatcc tgtccgtcca       180
agcagagacg caaaagctca tttctgaaat cgacttgttg cggaaacaaa acgaacagtt       240
gaaacacaaa cttgaacagc tgcggaactc ttgtgcgggc ggggggggtt ctggtggagg       300
aggaagcggt ggaggtgggt ctcctgcagc aaaacgggtg aaacttgatt aatgatag        358
```